United States Patent [19]

Desai

[11] Patent Number: 6,121,521
[45] Date of Patent: Sep. 19, 2000

[54] CHIMERIC INSECTICIDAL PROTEIN AND DNA CODING THEREFOR

[75] Inventor: Nalini M. Desai, Cary, N.C.

[73] Assignee: Novartis AG, Basel, Switzerland

[21] Appl. No.: 09/053,549

[22] Filed: Apr. 1, 1998

[51] Int. Cl.[7] .............................. A01H 5/00; C12N 1/21; C12N 5/14; C12N 15/32; C12N 15/82
[52] U.S. Cl. ................................ 800/320.1; 435/252.3; 435/320.1; 435/419; 536/23.71; 800/302
[58] Field of Search .......................... 435/172.3, 320.1, 435/419, 69.1, 468, 252.3; 800/205, 279, 302, 320.1; 536/23.71

[56] References Cited

U.S. PATENT DOCUMENTS

| | | | |
|---|---|---|---|
| 5,380,831 | 1/1995 | Adang et al. | 536/23.71 |
| 5,436,391 | 7/1995 | Fujimoto et al. | 800/205 |
| 5,593,881 | 1/1997 | Thompson et al. | 435/240.1 |
| 5,625,136 | 4/1997 | Koziel et al. | 800/205 |
| 5,628,995 | 5/1997 | Peferoen et al. | 424/93.21 |
| 5,736,131 | 4/1998 | Bosch et al. | 424/93.2 |

FOREIGN PATENT DOCUMENTS

| | | |
|---|---|---|
| 0290395 | 11/1988 | European Pat. Off. |
| 0348348 | 12/1989 | European Pat. Off. |
| 0353908 | 2/1990 | European Pat. Off. |
| 0359472 | 3/1990 | European Pat. Off. |
| 0374753 | 6/1990 | European Pat. Off. |
| 0385962 | 9/1990 | European Pat. Off. |
| 0408403 | 1/1991 | European Pat. Off. |
| 0431829 | 6/1991 | European Pat. Off. |
| 90/10076 | 9/1990 | WIPO. |
| 91/10725 | 7/1991 | WIPO. |
| 91/16432 | 10/1991 | WIPO. |
| 93/07278 | 4/1993 | WIPO. |

OTHER PUBLICATIONS

Fischhoff, et al., *Bio/Technology* 5: 807–813 (1987).
Murray, et al., *Nucleic Acids Research* 17(2): 477–498 (1989).
Vaeck, et al., *Nature* 328: 33–37 (1987).
Barton et al., Plant Physiol. (1987) 85, 1103–1109.
Brizzard and Whitely, Nucleic Acids Research, vol. 16, No. 6, 1988, 2723–2724.
Geiser et al., Gene, 48 (1986) 109–118.
Hofte and Whitely, MicroBiological Reviews, Jun. 1989, 242–255.
Koziel et al, Bio/Technology, vol. 11, Feb. 1993, 194–200.
Ohta et al., Mol Gen Genet, (1991) 225:369–378.
Perlak et al., Proc. Natl. Acad. Sci., USA, vol. 88, 3324–3328, Apr. 1991.

*Primary Examiner*—Lynette R. F. Smith
*Assistant Examiner*—Amy J. Nelson
*Attorney, Agent, or Firm*—J. Timothy Meigs; Gary M. Pace

[57] ABSTRACT

The present invention describes the design and construction of a chimeric insecticidal protein by joining the 5' portion of a synthetic maize optimized cry1B gene (SFLIB) to the 3' end of a full-length synthetic maize optimized cry1A(b) gene to generate a full-length hybrid cry1B gene (hyFLIB). When the chimeric insecticidal protein gene is expressed in transgenic maize from both PEPC and pith promoters, insecticidal activity is observed in transgenic maize tissue against European corn borer (*Ostrinia nubilalis*). An additional aspect of the invention is recombinant, biologically pure microbial strains transformed with the hyFLIB gene which can be used in entomocidal formulations for the control of Lepidopteran insects. Yet another aspect of the invention is plants transformed with the toxin gene or active fragments thereof, particularly where the transforming sequences have been optimized for expression in maize.

22 Claims, 9 Drawing Sheets ic*

CHIMERIC INSECTICIDAL PROTEIN AND DNA CODING THEREFOR

BACKGROUND OF THE INVENTION

*Bacillus thuringiensis* belongs to the large group of gram-positive, aerobic, endospore-forming bacteria. Unlike other very closely related species of Bacillus such as *B. cereus* or *B. anthracis*, the majority of the hitherto known *Bacillus thuringiensis* species produce in the course of their sporulation a parasporal inclusion body which, on account of its crystalline structure, is generally referred to also as a crystalline body. This crystalline body is composed of insecticidally active crystalline protoxin proteins, the so-called δ-endotoxins.

These protein crystals are responsible for the toxicity to insects of *Bacillus thuringiensis*. The δ-endotoxin does not exhibit its insecticidal activity until after oral intake of the crystalline body, when the latter is dissolved in the intestinal juice of the target insects. In most cases the actual toxic component is released from the protoxin as a result of proteolytic cleavage caused by the action of proteases from the digestive tract of the insects.

The δ-endotoxins of the various *Bacillus thuringiensis* strains are characterized by high specificity with respect to certain target insects, especially with respect to various Lepidoptera, Coleoptera and Diptera larvae, and by a high degree of activity against these larvae. A further advantage in using δ-endotoxins of *Bacillus thuringiensis* resides in the fact that the toxins are harmless to humans, other mammals, birds and fish.

With the introduction of genetic engineering and the new possibilities resulting from it, the field of *Bacillus thuringiensis* toxins has received a fresh impetus. For example, it is known that many naturally-occurring strains possess more than one insect toxin protein, which may account for a wide spectrum of insecticidal activity of those strains. However, with the ability to genetically transform Bacillus it is possible to create recombinant strains which may contain a chosen array of insect toxin genes obtained by isolation and cloning from naturally-occurring sources. Such recombinant strains can be made to provide whatever spectrum of insecticidal activity might be desired for a particular application, based upon a knowledge of the insecticidal activity of individual toxin proteins. Furthermore, it is also possible to create recombinant toxin proteins which have a chosen combination of functions designed to enhance the degree of insecticidal activity against a particular insect or insect class, or to expand the spectrum of insects against which the toxin protein is active.

The various naturally-occurring insecticidal crystal proteins from *Bacillus thuringiensis* have been classified based upon their spectrum of activity and sequence similarity. The classification put forth by Höfte and Whiteley, Microbiol. Rev. 53: 242–255 (1989) placed the then known insecticidal crystal proteins into four major classes. Generally, the major classes are defined by the spectrum of activity, with the CryI proteins active against Lepidoptera, CryII proteins active against both Lepidoptera and Diptera, CryIII proteins active against Coleoptera, and CryIV proteins active against Diptera.

Within each major class, the δ-endotoxins are grouped according to sequence similarity. The CryI proteins are typically produced as 130–140 kDa protoxin proteins which are proteolytically cleaved to produce active toxin proteins about 60–70 kDa. The active portion of the δ-endotoxin resides in the NH$_2$-terminal portion of the full-length molecule. Höfte and Whiteley, supra, classified the then known CryI proteins into six groups, IA(a), IA(b), IA(c), IB, IC, and ID. Since then, proteins classified as CryIE, CryIF, CryIG, and CryIX have also been characterized.

It is well known that many δ-endotoxin proteins from *Bacillus thuringiensis* are actually expressed as protoxins. To be insecticidal, these protoxins must first be ingested by the insect, solubilized in the alkaline environment of the insect gut and are proteolytically converted by proteases into a toxic core fragment (Höfte and Whiteley, Microbiol. Rev. 53: 242–255 (1989)). For δ-endotoxin proteins of the CryI class, the toxic core fragment is localized in the N-terminal half of the protoxin, whereas the C-terminal portion of the protoxin is proteolytically cleaved to form an active toxin. Chimeric insecticidal proteins can be constructed having novel sequences not found in nature by combining the toxin portion from one δ-endotoxin with the protoxin portion of a different δ-endotoxin.

SUMMARY OF THE INVENTION

Figure 1:
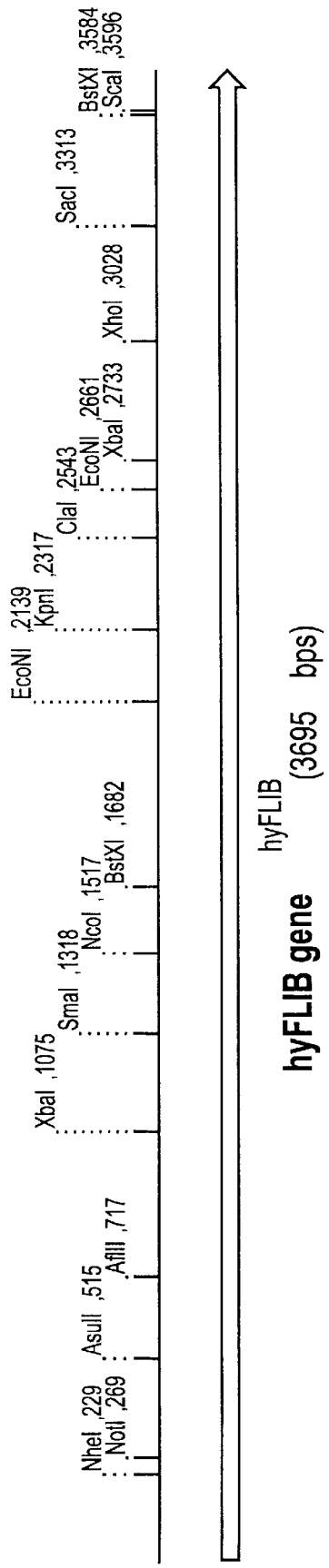
FIG. 1: A restriction map of the hyFLIB gene as set forth in SEQ ID NO:1.

Specifically, it is one of the objects of the present invention to provide synthetic insecticidal protein genes which have been optimized for expression in plants.

It is another object of the present invention to provide synthetic Bt insecticidal protein genes to maximize the expression of Bt proteins in a plant, preferably in a maize plant. It is one feature of the present invention that a synthetic Bt IP gene is constructed using the most preferred maize codons, except for alterations necessary to provide ligation sites for construction of the full synthetic gene.

Another object of the present invention is a chimeric insecticidal protein comprising a N-terminal toxin portion of the CryIB protein and the C-terminal protoxin portion of the CryIA(b) protein. In a preferred embodiment, a chimeric insecticidal protein comprises the amino acid sequence encoded by the 5' portion of a synthetic maize optimized cryIB gene (SFLIB) fused to the amino acid sequence encoded by the 3' portion of a synthetic maize optimized cryIA(b) gene. This protein is encoded by a full-length hybrid cryIB gene and is designated "hyFLIB". In a particularly preferred embodiment, the chimeric insecticidal protein is that set forth in SEQ ID NO: 2, and is encoded by the coding sequence set forth in SEQ ID NO: 1.

An additional aspect of the invention is recombinant, biologically pure microbial strains transformed with the hyFLIB gene which can be used in entomocidal formulations for the control of Lepidopteran insects. Yet another aspect of the invention are plants transformed with the toxin gene or active fragments thereof, particularly where the transforming sequences have been optimized for expression in maize.

DETAILED DESCRIPTION OF THE INVENTION

According to the above objects, we have synthesized Bt insecticidal crystal protein genes in which the codon usage has been altered in order to increase expression in plants, particularly maize. However, rather than alter the codon usage to resemble a maize gene in terms of overall codon distribution, we have optimized the codon usage by using the codons which are most preferred in maize (maize preferred codons) in the synthesis of the synthetic gene. The optimized maize preferred codon usage is effective for expression of high levels of the Bt insecticidal protein. This might be the result of maximizing the amount of Bt insecticidal protein translated from a given population of messenger RNAs. The synthesis of a Bt gene using maize preferred codons also tends to eliminate fortuitous processing sites that might occur in the native coding sequence. The expression of this synthetic gene is significantly higher in maize cells than that of the native IP Bt gene.

Preferred synthetic, maize optimized DNA sequences of the present invention derive from the protein encoded by the cryIA(b) gene in *Bacillus thuringiensis* var. kurstaki, HD-1; Geiser et al., *Gene*, 48:109–118 (1986) or the cryIB gene (AKA Crya4 gene) described by Brizzard and Whiteley, *Nuc. Acids. Res.*, 16:2723 (1988).

The following definitions are provided in order to provide clarity with respect to the terms as they are used in the specification and claims to describe the present invention.

Maize preferred codon: Preferred codon refers to the preference exhibited by a specific host cell in the usage of nucleotide codons to specify a given amino acid. The preferred codon for an amino acid for a particular host is the single codon which most frequently encodes that amino acid in that host. The maize preferred codon for a particular amino acid may be derived from known gene sequences from maize. For example, maize codon usage for 28 genes from maize plants are listed in Table 4 of Murray et al., *Nucleic Acids Research*, 17:477–498 (1989), the disclosure of which is incorporated herein by reference. For instance, the maize preferred codon for alanine is GCC, since, according to pooled sequences of 26 maize genes in Murray et al., supra, that codon encodes alanine 36% of the time, compared to GCG (24%), GCA (13%), and GCT (27%).

Pure maize optimized sequence: An optimized gene or DNA sequence refers to a gene in which the nucleotide sequence of a native gene has been modified in order to utilize preferred codons for maize. For example, a synthetic maize optimized Bt cryIA(b) gene is one wherein the nucleotide sequence of the native Bt cryIA(b) gene has been modified such that the codons used are the maize preferred codons, as described above. A pure maize optimized gene is one in which the nucleotide sequence comprises 100 percent of the maize preferred codon sequences for a particular polypeptide. For example, the pure maize optimized Bt cryIA(b) gene is one in which the nucleotide sequence comprises 100 percent maize preferred codon sequences and encodes a polypeptide with the same amino acid sequence as that produced by the native Bt cryIA(b) gene. The pure nucleotide sequence of the optimized gene may be varied to permit manipulation of the gene, such as by altering a nucleotide to create or eliminate restriction sites. The pure nucleotide sequence of the optimized gene may also be varied to eliminate potentially deleterious processing sites, such as potential polyadenylation sites or intron recognition sites.

It is recognized that "partially maize optimized," sequences may also be utilized. By partially maize optimized, it is meant that the coding region of the gene is a chimeric (hybrid), being comprised of sequences derived from a native insecticidal gene and sequences which have been optimized for expression in maize. A partially optimized gene expresses the insecticidal protein at a level sufficient to control insect pests, and such expression is at a higher level than achieved using native sequences only. Partially maize optimized sequences include those which contain at least about 5% optimized sequences.

Full-length Bt Genes: Refers to DNA sequences comprising the full nucleotide sequence necessary to encode the polypeptide produced by a native Bt gene. For example, the native Bt cryIA(b) gene is approximately 3.5 Kb in length and encodes a polypeptide which is approximately 1150 amino acids in length. A full-length synthetic cryIA(b) Bt gene would be at least approximately 3.5 Kb in length.

Truncated Bt Genes: Refers to DNA sequences comprising less than the full nucleotide sequence necessary to encode the polypeptide produced by a native Bt gene, but which encodes the active toxin portion of the polypeptide. For example, a truncated synthetic Bt gene of approximately 1.9 Kb encodes the active toxin portion of the polypeptide such that the protein product exhibits insecticidal activity.

The present invention encompasses maize optimized coding sequences according to the teachings of U.S. Pat. No. 5,625,136, herein incorporated by reference in its entirety. Also encompassed by the invention are encoding other polypeptides, including those of other *Bacillus thuringiensis* insecticidal polypeptides or insecticidal proteins from other sources. For example, cryIB genes can be maize optimized, and then stably introduced into plants, particularly maize. The sequence of a maize optimized cryIB gene constructed in accordance with the present invention is set forth in SEQ ID NO:7.

The present invention encompasses a unique chimeric insecticidal protein which is created by replacing all or part of the native protoxin segment with an alternate protoxin segment. In a preferred embodiment, the chimeric insecticidal protein comprises a CryIA(b) C-terminal protoxin portion and a CryIB core N-terminal toxin portion. A particularly preferred embodiment comprises a synthetic maize optimized cryIB gene (SFLIB) at the 3' end of the full-length synthetic maize optimized cryIA(b) gene to generate a full-length hybrid cryIB gene (hyFLIB). This unique chimeric insecticidal protein has the full toxin portion of CryIB (amino acids 1–845) and a portion of the CryIA(b) protoxin portion (amino acids 846–1227). When the chimeric insecticidal protein gene is expressed in transgenic maize from both PEPC and pith promoters, insecticidal activity is observed in transgenic maize tissue against European corn borer (*Ostrinia nubilalis*).

An additional aspect of the invention is recombinant, biologically pure microbial strains transformed with the hyFLIB gene which can be used in entomocidal formulations for the control of Lepidopteran insects. Yet another aspect of the invention are plants transformed with the toxin gene or active fragments thereof, particularly where the transforming sequences have been optimized for expression in maize.

Recombinant Microorganisms Comprising the Novel Toxin Gene and Protein

It should also be recognized that the isolated novel toxin gene of the present invention can be transferred into any microbial host and confer its insecticidal properties upon that host. Alternate hosts for the novel toxin gene of the present invention can be selected as suitable for cloning purposes, for purposes of characterizing the form and function of the gene or encoded protein, for use as a fermentation host to increase production of the toxin protein, for purposes of delivering the toxin protein more effectively to the target insect pest, or introduction of the novel toxin gene into insect pathogens such as baculovirus to improve their effectiveness.

The novel toxin gene or recombinant forms thereof can be transformed into such alternate hosts using a variety of art recognized methods. One such preferred method is electroporation of microbial cells, as described, for example, by the method of Dower (U.S. Pat. No. 5,186,800). Another preferred method is that of Schurter et al. (Mol. Gen. Genet. 218: 177–181 (1989)), which is also disclosed in U.S. Ser. No. 07/353,565 which is incorporated herein in its entirety.

It is envisioned that said alternate host would be applied to the environment or plants or animals for insect control. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Bacillus, Caulobacter, Agmenellum, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as Bacillus spp., Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli and Azotobacter vinlandii; and phytosphere yeast species such as Rhodotorula rubra, R. glutinis, R. marina, R. aurantiaca, Cryptococcus albidus, C. diffluens, C. laurentii Saccharomyces rosei, S. pretoriensis, S. cerevisiae, Sporobolomyces rosues, S. odorus, Kluyveromyces veronae, and Aureobasidium pollulans. Of particular interest are the pigmented microorganisms.

The present invention further provides an entomocidal composition comprising a recombinant Bacillus thuringiensis strain containing the novel toxin gene in recombinant form, or a derivative or mutant thereof, together with an agricultural adjuvant such as a carrier, diluent, surfactant or application-promoting adjuvant. The composition may also contain a further biologically active compound selected from fertilizers, micronutrient donors, plant growth preparations, herbicides, insecticides, fungicides, bactericides, nematicides and molluscicides and mixtures thereof. The composition may comprise from 0.1 to 99% by weight of the recombinant Bacillus thuringiensis strain containing the novel gene in recombinant form, or the derivative or mutant thereof, from 1 to 99.9% by weight of a solid or liquid adjuvant, and from 0 to 25% by weight of a surfactant. The recombinant Bacillus thuringiensis strain containing the novel gene in recombinant form, or the composition containing it, may be administered to the plants or crops to be protected together with certain other insecticides or chemicals (1993 Crop Protection Chemicals Reference, Chemical and Pharmaceutical Press, Canada) without loss of potency. It is compatible with most other commonly used agricultural spray materials but should not be used in extremely alkaline spray solutions. It may be administered as a dust, a suspension, a wettable powder or in any other material form suitable for agricultural application.

Target crops to be protected within the scope of the present invention comprise, e.g., the following species of plants:

cereals (wheat, barley, rye, oats, rice, sorghum and related crops), beet (sugar beet and fodder beet), forage grasses (orchardgrass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), citrus fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

Entomocidal Compositions Comprising a Recombinant Bacillus thuringiensis Strain

The recombinant Bacillus thuringiensis strain containing the novel gene in recombinant form is normally applied in the form of entomocidal compositions and can be applied to the crop area or plant to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The formulations, i.e. the entomocidal compositions, preparations or mixtures containing the recombinant Bacillus thuringiensis strain containing the novel gene in recombinant form as an active ingredient or combinations thereof with other active ingredients, and, where appropriate, a solid or liquid adjuvant, are prepared in known manner, e.g., by homogeneously mixing and/or grinding the active ingredients with extenders, e.g., solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used, e.g., for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds. Suitable soaps are the alkali metal salts, alkaline earth metal salts or unsubstituted or substituted ammonium salts of higher fatty acids (C sub 10 –C sub 22), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates. The fatty sulfonates or sulfates are usually in the forms of alkali metal salts, alkaline earth metal salts or unsubstituted or substituted ammonium salts and generally contain a C sub 8 –C sub 22 alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide. Non-ionic surfactant are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one C sub 8 –C sub 22 alkyl radical and, as further substituents, lower unsubstituted or halogenated alkyl, benzyl or hydroxyl-lower alkyl radicals. The salts are preferably in the form of halides, methylsulfates or ethylsulfates, e.g., stearyltrimethylammonium chloride or benzyldi-(2-chloroethyl) ethylammonium bromide.

The surfactants customarily employed in the art of formulation are described, e.g., in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna.

Another particularly preferred characteristic of an entomocidal composition of the present invention is the persistence of the active ingredient when applied to plants and soil. Possible causes for loss of activity include inactivation by ultra-violet light, heat, leaf exudates and pH. For example, at high pH, particularly in the presence of reductant, δ-endotoxin crystals are solubilized and thus become more accessible to proteolytic inactivation. High leaf pH might also be important, particularly where the leaf surface can be in the range of pH 8–10. Formulation of an entomocidal composition of the present invention can address these problems by either including additives to help prevent loss of the active ingredient or encapsulating the material in such a way that the active ingredient is protected from inactivation. Encapsulation can be accomplished chemically (McGuire and Shasha, 1992) or biologically (Barnes and Cummings, 1986). Chemical encapsulation involves a process in which the active ingredient is coated with a polymer while biological encapsulation involves the expression of the δ-endotoxin genes in a microbe. For biological encapsulation, the intact microbe containing the δ-endotoxin protein is used as the active ingredient in the formulation. The addition of UV protectants might effectively reduce irradiation damage. Inactivation due to heat could also be controlled by including an appropriate additive.

The entomocidal compositions usually contain 0.1 to 99%, preferably 0.1 to 95%, of the recombinant *Bacillus thuringiensis* strain containing the novel gene in recombinant form, or combination thereof with other active ingredients, 1 to 99.9% of a solid or liquid adjuvant, and 0 to 25%, preferably 0.1 to 20%, of a surfactant. Whereas commercial products are preferably formulated as concentrates, the end user will normally employ dilute formulations of substantially lower concentration. The entomocidal compositions may also contain further ingredients, such as stabilizers, antifoams, viscosity regulators, binders, tackifiers as well as fertilizers or other active ingredients in order to obtain special effects.

Transgenic Plants Comprising the Novel Toxin Gene or Protein

A host plant expressing at least one of the novel toxin genes of the invention will have enhanced resistance to insect attack and will be thus better equipped to withstand crop losses associated with such attack. By plant is meant any plant species which can be genetically transformed by methods known in the art. Methods known in the art for plant transformation are discussed below. Host plants include, but are not limited to, those species previously listed as target crops.

It has been discovered that the codon usage of a native *Bacillus thuringiensis* toxin gene is significantly different from that which is typical of a plant gene. In particular, the codon usage of a native *Bacillus thuringiensis* gene is very different from that of a maize gene. As a result, the mRNA from this gene may not be efficiently utilized. Codon usage might influence the expression of genes at the level of translation or transcription or mRNA processing. To optimize a toxin gene for expression in plants, for example in maize, the codon usage is optimized by using the codons which are most preferred in maize (maize preferred codons) in the synthesis of a synthetic gene which encodes the same protein as found for the native toxin gene sequence. The optimized maize preferred codon usage is effective for expression of high levels of the Bt insecticidal protein. Further details for constructing maize-optimized synthetic toxin genes can be found in U.S. Pat. No. 5,625,136, herein incorporated by reference in its entirety.

Toxin genes derived from microorganisms may also differ from plant genes. Plant genes differ from genes found in microorganisms in that their transcribed RNA does not possess defined ribosome binding site sequence adjacent to the initiating methionine. Consequently, microbial genes can be enhanced by the inclusion of a eukaryotic consensus translation initiator at the ATG. Clontech (1993/1994 catalog, page 210) has suggested the sequence GTCGACC ATGGTC as a consensus translation initiator for the expression of the *E. coli* uidA gene in plants. Further, Joshi (Nucl Acids Res 15: 6643–6653,1987) has compared many plant sequences adjacent to the ATG and suggests the consensus TAAACAATGGCT. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. By surveying the sequence of maize genes present in the GenBank/EMBL database it can be discerned which nucleotides adjacent to the ATG should be modified to enhance translation of the toxin gene introduced into maize.

In addition, it has been shown that removal of illegitimate splice sites can enhance expression and stability of introduced genes. Genes cloned from non-plant sources and not optimized for expression in plants may contain motifs which can be recognized in plants as 5' or 3' splice sites. Consequently, the transcription process can be prematurely terminated, generating truncated or deleted mRNA. The toxin genes can be engineered to remove these illegitimate splice sites using techniques known in the art.

It is within the scope of the present invention that genes encoding either the full-length protoxin form or the truncated toxic core fragment of the novel toxin proteins can be used in plant transformation vectors to confer insecticidal properties upon the host plant.

The recombinant DNA molecules can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., BioTechniques 4:320–334 (1986)), electroporation (Riggs et al, Proc. Natl. Acad. Sci. USA 83:5602–5606 (1986), Agrobacterium-mediated transformation (Hinchee et al., Biotechnology 6:915–921 (1988)), direct gene transfer (Paszkowski et al., EMBO J. 3:2717–2722 (1984)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6:923–926 (1988); see also Weissinger et al., Annual Rev. Genet. 22:421–477 (1988); Sanford et al., Particulate Science and Technology 5:27–37 91987)(onion); Christou et al., Plant Physiol. 87:671–674 (1988)(soybean); McCabe et al., Bio/Technology 6:923–926 (1988)(soybean); Datta et al., Bio/Technology 8:736–740 (1990)(rice); Klein et al., Proc. Natl. Acad. Sci. USA, 85:4305–4309 (1988)(maize); Klein et al., Bio/Technology 6:559–563 (1988)(maize); Klein et al., Plant Physiol. 91:440–444 (1988)(maize); Fromm et al., Bio/Technology 8:833–839 (1990); and Gordon-Kamm et al., Plant Cell 2:603–618 (1990)(maize); Svab et al. Proc. Natl. Acad. Sci. USA 87: 8526–8530 (1990) (tobacco chloroplast); Koziel et al. (Biotechnology 11: 194–200 (1993)) (maize); Shimamoto et al. Nature 338: 274–277 (1989) (rice); Christou et al. Biotechnology 9: 957–962 (1991) (rice); European Patent Application EP 0 332 581 (orchardgrass and other Pooideae); Vasil et al. (Biotechnology 11: 1553–1558 (1993) (wheat); Weeks et al. (Plant Physiol. 102: 1077–1084 (1993) (wheat); Wan et al. (Plant Physiol. 104: 37–48 (1994)(barley)); Umbeck et al., (Bio/Technology 5: 263–266 (1987)(cotton).

One particularly preferred set of embodiments for the introduction of recombinant DNA molecules into maize by microprojectile bombardment. An additional preferred embodiment is the protoplast transformation method for maize as disclosed in U.S. Pat. No. 5,350,689, hereby incorporated by reference in its entirety.

Transformation of plants can be undertaken with a single DNA species or multiple DNA species (i.e. co-transformation) and both these techniques are suitable for use with the novel toxin gene of the present invention.

Methods using either a form of direct gene transfer or Agrobacterium-mediated transfer usually, but not necessarily, are undertaken with a selectable marker which may provide resistance to an antibiotic (kanamycin, hygromycin or methotrexate) or a herbicide (phosphinothricin). The choice of selectable marker for plant transformation is not, however, critical to the invention.

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19: 259–268 (1982); Bevan et al., Nature 304:184–187 (1983)), the bar gene which confers resistance to the herbicide phosphinothricin (White et al., Nucl Acids Res 18: 1062 (1990), Spencer et al. Theor Appl Genet 79: 625–631(1990)), the hph gene which confers resistance to the antibiotic hygromycin (Blochinger & Diggelmann, Mol Cell Biol 4: 2929–2931), the dhfr gene, which confers resistance to methotrexate (Bourouis et al., EMBO J. 2: 1099–1104 (1983), and the mannose phosphate isomerase (PMI) gene, which allows selection on mannose as a carbon source (EP 530 129, WO 94/20627)

Many vectors are available for transformation using *Agrobacterium tumefaciens*. These typically carry at least one T-DNA border sequence and include vectors such as pBIN19 (Bevan, Nucl. Acids Res. (1984)). In one preferred embodiment, the novel toxin gene of the present invention may be inserted into either of the binary vectors pCIB200 and pCIB2001 for use with Agrobacterium. These vector cassettes for Agrobacterium-mediated transformation can be constructed in the following manner. pTJS75kan was created by NarI digestion of pTJS75 (Schmidhauser & Helinski, J Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also EP 0 332 104, example 19). pCEB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

An additional vector useful for Agrobacterium-mediated transformation is the binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 have been constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

Other transformation techniques which do not rely on Agrobacterium, the so-called direct gene transfer methods, are also useful for the introduction of the novel toxin gene of the present invention, including transformation by microprojectile bombardment, protoplast uptake (e.g. PEG and electroporation) and microinjection. The choice of vector for these methods depends largely on the preferred selection for the species being transformed.

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in the PCT published application WO 93/07278, herein incorporated by reference. The gene providing resistance to phosphinothricin is the bar gene from *Streptomyces hygroscopicus* (Thompson et al. EMBO J 6: 2519–2523 (1987)). This vector is suitable for the cloning of plant expression cassettes containing their own regulatory signals.

An additional transformation vector is pSOG35 which utilizes the *E. coli* gene dihydrofolate reductase (DHFR) as a selectable marker conferring resistance to methotrexate. PCR was used to amplify the 35S promoter (~800 bp), intron 6 from the maize Adhl gene (~550 bp; see Dennis et al., Nucleic Acid Res. 12:3983–4000 (1984)) and 18 bp of the GUS untranslated leader sequence (see Jefferson et al., Proc. Nat. Acad. Sci. USA 83: 8447–8451 (1986). A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus check (MCMV) generated the vector pSOG35. pSOG19 and pSOG35 carry the pUC gene for ampicillin resistance and have HindIII, SphI, PstI and EcoRI sites available for the cloning of foreign sequences.

The coding sequence of the novel insecticidal proteins of the present invention can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. Preferred constitutive promoters include the CaMV 35S and 19S promoters (Fraley et al., U.S. Pat. No. 5,352,605, issued Oct. 4, 1994). An additionally preferred promoter is derived from any one of several of the actin genes, which are known to be expressed in most cell types. The promoter expression cassettes described by McElroy et al. (Mol. Gen. Genet. 231: 150–160 (1991)) can be easily modified for the expression of the novel toxin gene and are particularly suitable for use in monocotyledonous hosts.

Yet another preferred constitutive promoter is derived from ubiquitin, which is another gene product known to accumulate in many cell types. The ubiquitin promoter has been cloned from several species for use in transgenic plants (e.g. sunflower—Binet et al. Plant Science 79: 87–94 (1991), maize—Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel toxin gene in plants, particularly maize, are those which direct expression in root, pith, leaf or pollen. Such promoters, e.g. those isolated from PEPC or trpA, are disclosed in U.S. Pat. No. 5,625,136, or MTL, disclosed in U.S. Pat. No. 5,466,785. Both U.S. patents are herein incorporated by reference in their entirety. Chemically inducible promoters useful for directing the expression of the novel toxin gene in plants are disclosed in U.S. Pat. No. 5,614,395, herein incorporated by reference in its entirety.

In addition to promoters, a variety of transcriptional terminators are also available for use in chimeric gene construction using the novel toxin gene of the present invention. Transcriptional terminators are responsible for the termination of transcription beyond the transgene and its correct polyadenylation. Appropriate transcriptional terminators and those which are known to function in plants include the CaMV 35S terminator, the tml terminator, the nopaline synthase terminator, the pea rbcS E9 terminator and others known in the art. These can be used in both monocotyledons and dicotyledons.

Numerous sequences have also been found to enhance gene expression from within the transcriptional unit and these sequences can be used in conjunction with the novel toxin gene of this invention to increase their expression in transgenic plants.

Various intron sequences have been shown to enhance expression, particularly in monocotyledonous cells. For example, the introns of the maize Adhl gene have been found to significantly enhance the expression of the wild-type gene under its cognate promoter when introduced into maize cells (Callis et al., Genes Develop. 1: 1183–1200 (1987)). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15; 65–79 (1990)).

EXAMPLES

The following examples further describe the materials and methods used in carrying out the invention and the subsequent results. They are offered by way of illustration, and their recitation should not be considered as a limitation of the claimed invention.

Example 1
Construction of a Maize Optimized cryIB Full-length Hybrid Gene

CryIB is a δ-endotoxin of 1207 amino acids and is approximately 130 Kd in size. To design a synthetic cryIB gene, the deduced peptide sequence of CryIB (Brizzard & Whiteley, Nucl Acids Res. 16:2723, 1988) (Genbank accession number X06711) was backtranslated using the "Back-translation" program found in the University of Wisconsin GCG group of programs using a maize preference codon table (Murray et al., Nucl Acids Res. 17:477–498, 1989). By inserting unique restriction sites to facilitate cloning, the "maize optimized" sequence was further modified resulting in a synthetic full-length cryIB sequence (SFLIB). This gene was designed for cloning from 12 parts.

Each fragment of the synthetic gene was constructed by hybridization of 5–7 pairs of oligomers 60–75 nucleotides (nt) in length representing both strands of the gene. A 15 nt overlap was designed between sequential oligonucleotide pairs for correct orientation and assembly. The ends of each fragment were designed to have ends cohesive with DNA digested with restriction enzyme EcoRI at the 5' end and HindIII at the 3' ends. Oligos were synthesized by either IDT Inc (Iowa) or Oligos etc.(Oregon). Fragments of the gene were constructed either by hybridization and ligation of the oligonucleotides and cloning into pUC18 vector digested with EcoRI and HindIfi or by PCR amplification. Amplification was carried out using an equimolar mixture of oligomers as the template and primers with sequence corresponding to the ends of the fragment. Taq polymerase was used in the reactions, following standard conditions from the supplier (Perkin-Elmer). The amplified DNA for each fragment was cloned into a T—vector made from pBSSK+® (Marchuk et al., Nucl Acids Res. 19:1154, 1991). Gene fragments with the correct sequence were joined using the overlapping restriction endonuclease sites. Approximately 2.5 Kb of the synthetic cryIB gene (including the complete toxin region) was subcloned behind the Lac Z promoter derived from pUC18 resulting in pCIB5518. The protein from $E.\ coli$ transformed with pCIB5518 was 100% active in bioassay against ECB ($Ostrinia\ nubilalis$).

Eight of these fragments make up 2.54 Kb of the cryIB gene, and end at a ClaI restriction site. This position in the cryIB gene corresponds to the analogous position (and restriction site) in the cryIA(b) gene (at the beginning of the thermostable element described by Geiser et al., Gene 48:109–118, 1986). Homology at the protein and amino acid level is 80% in the region beyond amino acid residue 850 in CryEB (and corresponding to amino acid residue 804 in CryIA(b) and the end of both genes.

The 2.54 Kb of the synthetic cryIB gene was joined to the 3' end of the full-length synthetic cryIA(b) described in U.S. Pat. No. 5,625,136, herein incorporated by reference (SEQ ID NOS: 3, 5). This has been referred to as the full-length hybrid cryIB gene (hyFLIB).

A restriction map of the hyFLIB gene is shown in FIG. 1, the nucleotide sequence of the coding region is set forth in SEQ ID NO:1, and the encoded protein sequence is set forth in SEQ ID NO:2.

Example 2
Maize Transformation Vectors Comprising the hyFLIB Gene

Figure 2:
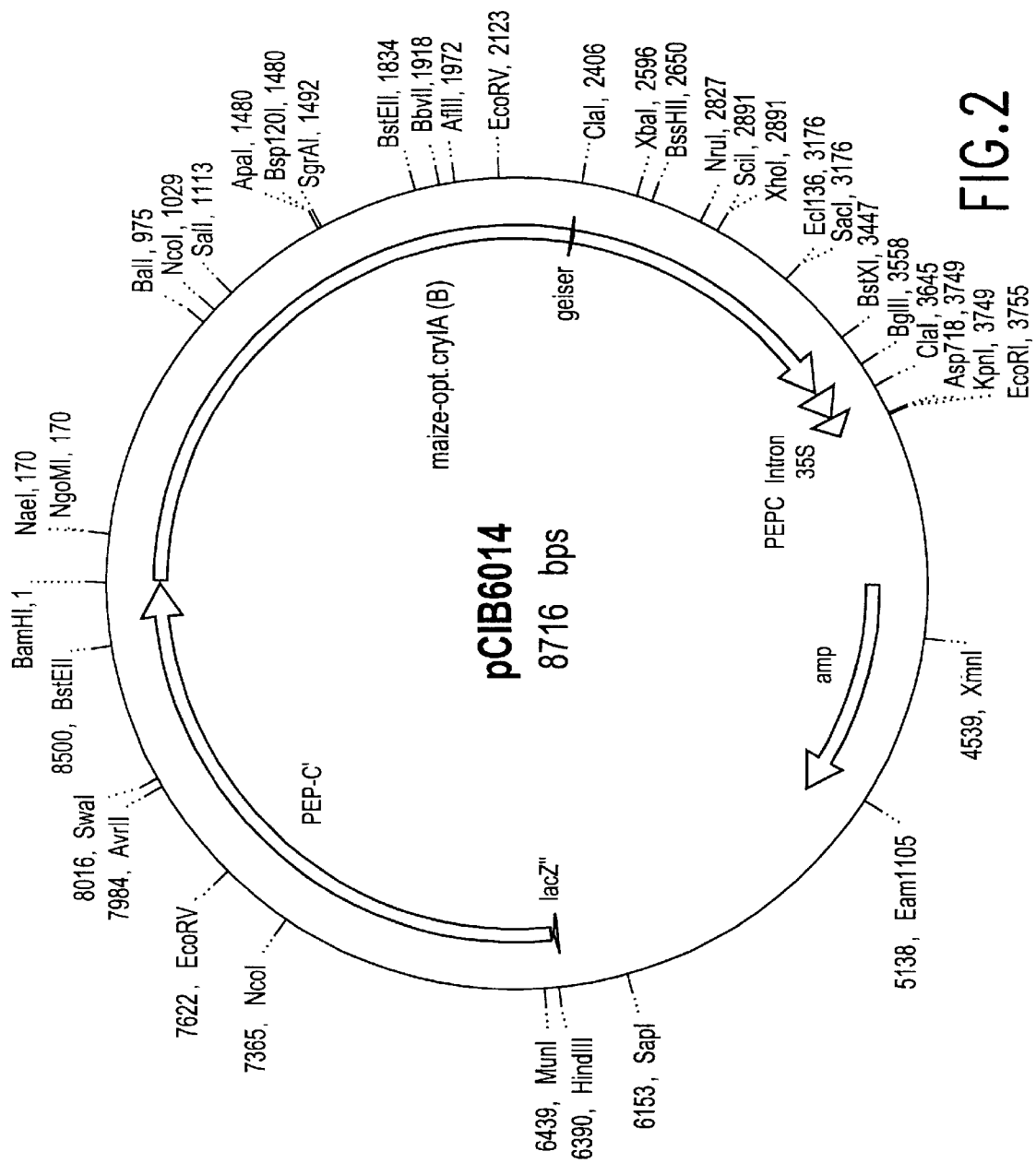
FIG. 2: Map of pCIB6014 used to make pCIB5520.
Figure 3:
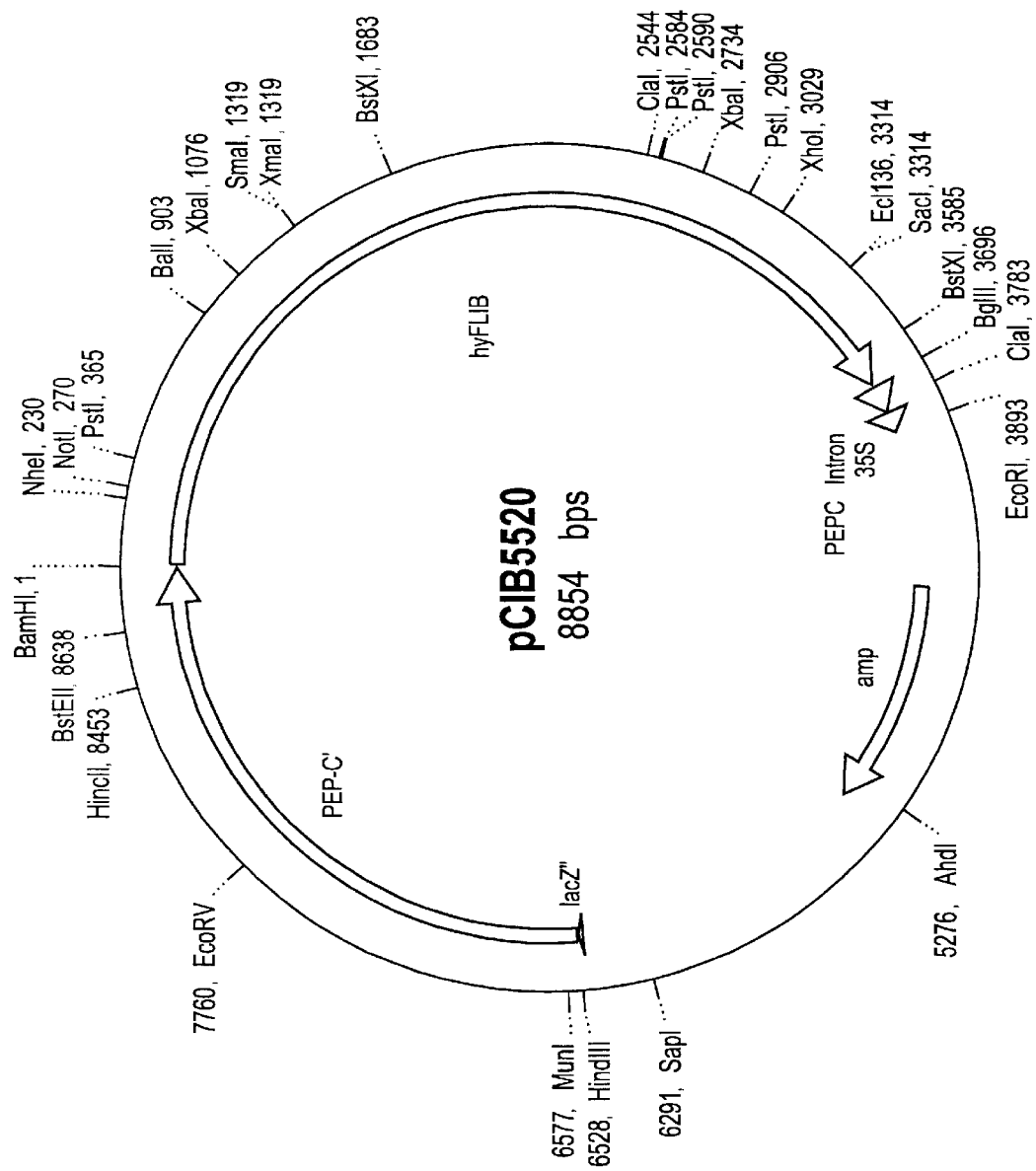
FIG. 3: Map of transforming plasmid pCIB5520 comprising the hyFLIB gene fused to the PEPC promoter.
Figure 4:
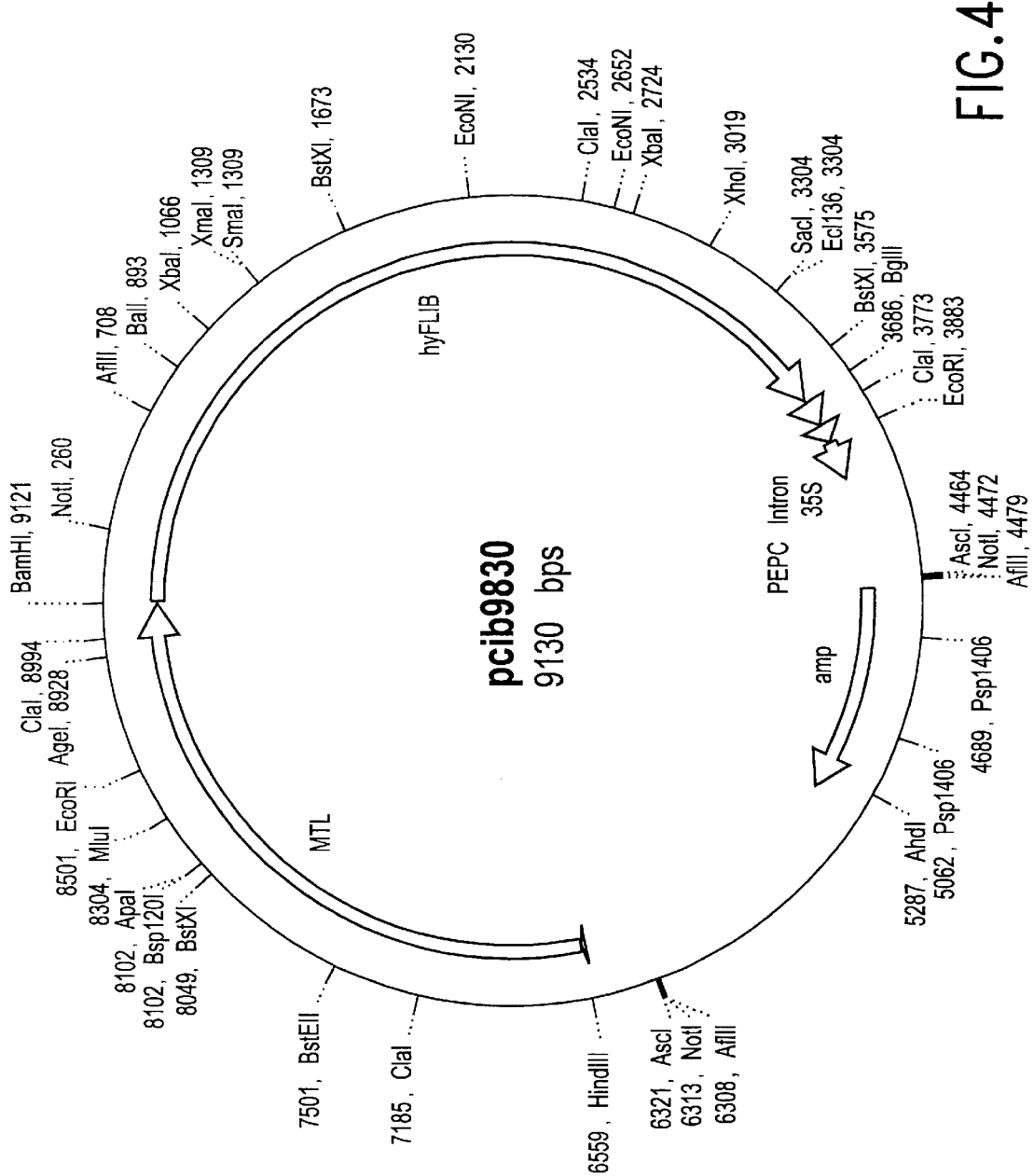
FIG. 4: Map of transforming plasmid pCIB9830 comprising the hyFLIB gene fused to the MTL promoter.
Figure 8:
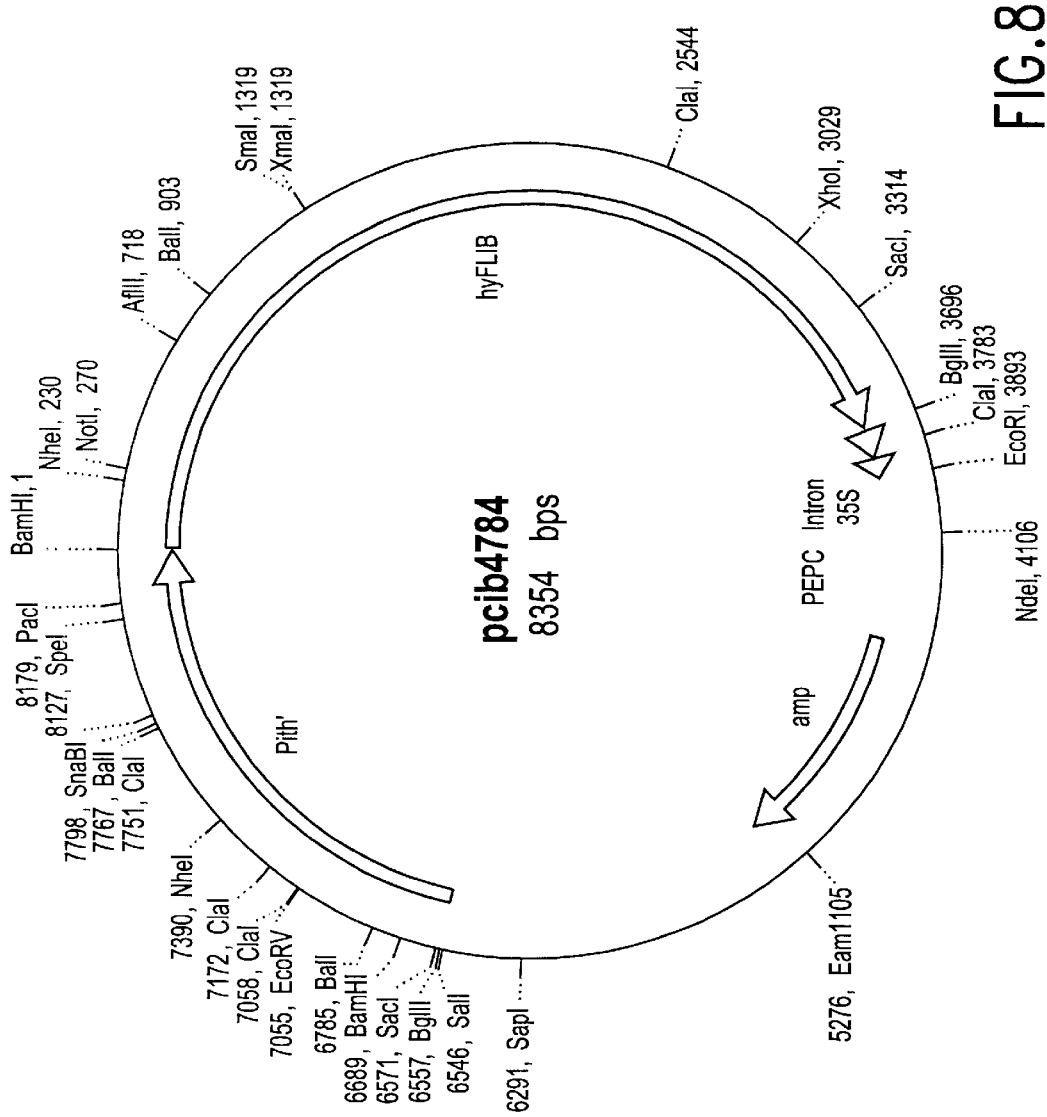
FIG. 8: Map of transforming plasmid pCIB4784 comprising the hyFLIB gene fused to the pith promoter.
Figure 9:
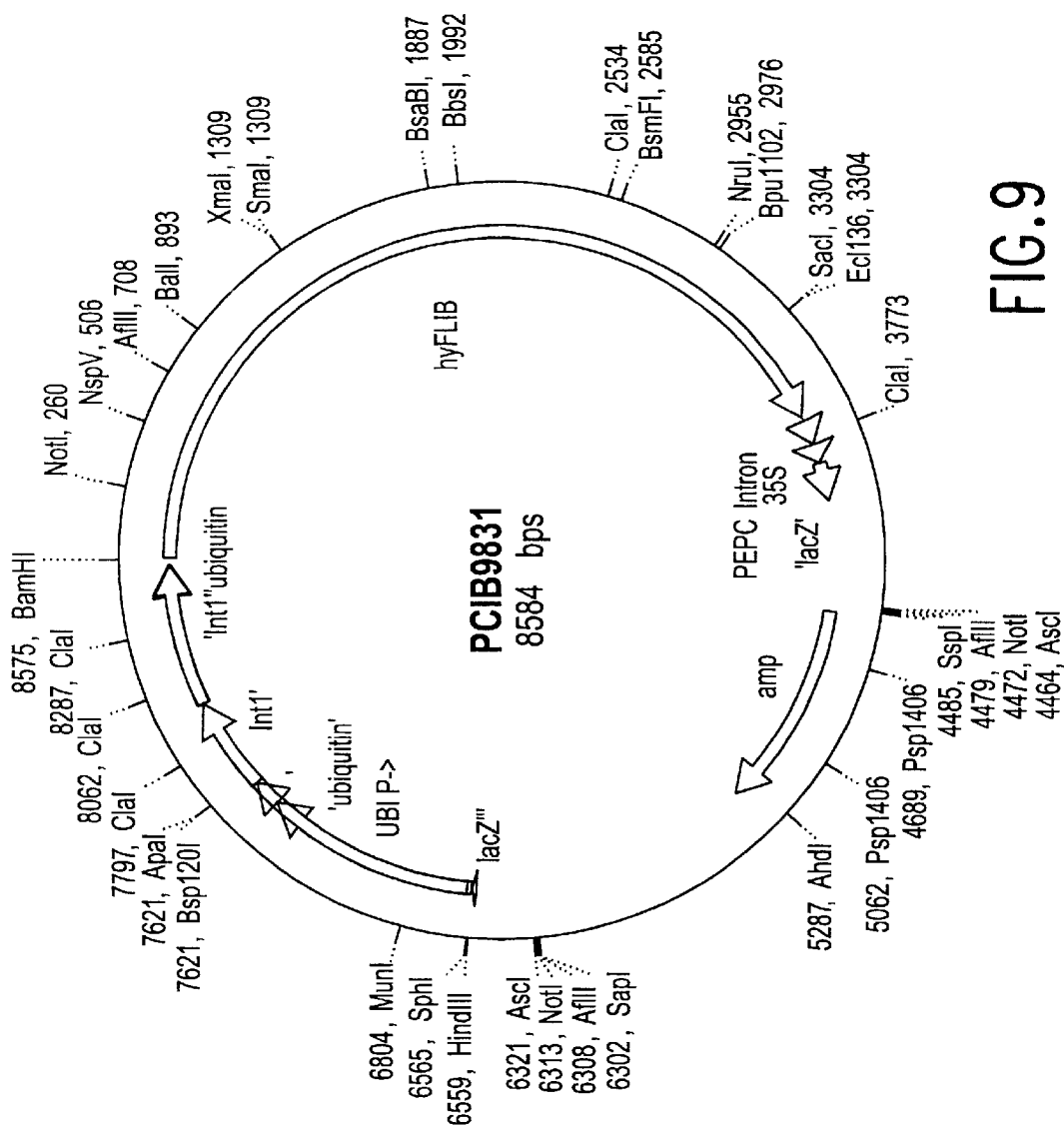
FIG. 9: Map of transforming plasmid pCIB9831 comprising the hyFLIB gene fused to the ubiquitin promoter.

For maize transformation, the 2.54 kb BamHI—ClaI fragment of the synthetic cryIB gene was cloned into pCEB6014 (FIG. 2) which contained the PEPC promoter and the full-length fully synthetic cryIA(b) gene (construction of the full-length synthetic cryLA(b) gene is set forth in U.S. Pat. No. 5,625,136, herein incorporated by reference), replacing the BamnHI—ClaI synthetic cryIA(b) fragment with the synthetic cryIB gene fragment described above and creating a full-length cryIB/cryIA(b) hybrid gene called hyFLIB. This full-length hybrid gene containing the PEPC promoter is called pCIB5520 (FIG. 3). The pCIB5520 clone was deposited under the terms of the Budapest Treaty on Apr. 1, 1998, with the Agricultural Research Service, Patent Culture Collection (NRRL), Northern Regional Research Center, 1815 Northern University Street, Peoria, Ill. 61604, U.S.A. and assigned accession number NRRL B-21972. The full-length hybrid gene was subcloned into plant expression vector cassettes containing the pith promoter, the MTL promoter and the maize ubiquitin promoter to give pCIB4784 (FIG. 8), pCIB9830 (FIG. 4) and pCIB9831 FIG. 9), respectively.

Example 3
Bioassay of Transformed Maize for Insecticidal Activity

Transformed plants were assayed for insecticidal activity and the presence of a BT protein resulting from the expression of the maize-optimized coding sequence of a synthetic BT gene. The procedure is similar for any maize plant transformed with a BT gene but is described here using as an example a cryIA(b) gene, its expressed product, and resistance to European corn borer.

Insecticidal activity was determined by insect bioassay. One to four 4 cm sections are cut from an extended leaf of a transformed maize plant. Each leaf piece is placed on a moistened filter disc in a 50×9 mm Petri dish. Five neonate European corn borer larvae are placed on each leaf piece. Since each plant is sampled multiple times this makes a total of 5–20 larvae per plant. The Petri dishes are incubated at 29.5° C. and leaf feeding damage and mortality data are scored at 48 hours.

EUROPEAN CORN BORER ASSAY

1. One to four 4 cm sections are cut from an extended leaf of a corn plant.
2. Each leaf piece is placed on a moistened filter disc in a 50×9 mm Petri dish.
3. Five neonate European corn borer larvae are placed on each leaf piece. (Making a total of 5–20 larvae per plant.)
4. The Petri dishes are incubated at 29.5° C.
5. Leaf feeding damage and mortality data are scored at 48 hours.

Example 4

Transformation of Maize with Novel Toxin Gene

Transformation of maize with at least one of the novel toxin genes prepared according to any of the above methods is achieved by microprojectile bombardment of either immature zygotic embryos or serially-propagatable Type I embryogenic callus.

Type I embryogenic callus cultures (Green et al, Miami Winter Symposium 20,1983) of the proprietary genotype CG00526 and CG00714 were initiated from immature embryos, 1.5–2.5 mm in length, from greenhouse grown material. Embryos were aseptically excised from surface-sterilized ears approximately 14 days after pollination. Embryos of CG00526 were placed on D callus initiation media with 2% sucrose and 5 mg/L chloramben (Duncan et al, Planta 165: 322–332,1985) while those of CG00714 were placed onto KM callus initiation media with 3% sucrose and 0.75 mg/L 2,4-d (Kao and Michayluk, Planta 126:105–110, 1975). Embryos and embryogenic cultures were subsequently cultured in the dark. Embryogenic responses were removed from the explants after ~14 days. CG00526 responses were placed onto D callus maintenance media with 2% sucrose and 0.5 mg/L 2,4-d while those of CG00714 were placed onto KM callus maintenance media with 2% sucrose and 5 mg/L Dicamba. After 3 to 8 weeks of weekly selective subculture to fresh maintenance media, high quality compact embryogenic cultures were established. Actively growing embryogenic callus pieces were selected as target tissue for gene delivery. The callus pieces were plated onto target plates containing maintenance medium with 12% sucrose approximately 4 hours prior to gene delivery. The callus pieces were arranged in circles, with radii of 8 and 10 mm from the center of the target plate.

Plasmid DNA was precipitated onto gold microcarriers as described in the DuPont Biolistics manual. Two to three jig of each plasmid was used in each 6 shot microcarrier preparation. Genes were delivered to the target tissue cells using the PDS-1000He Biolistics device. The settings on the Biolistics device were as follows: 8 mm between the rupture disc and the macrocarrier, 10 mm between the macrocarrier and the stopping screen and 7 cm between the stopping screen and the target. Each target plate was shot twice using 650 psi rupture discs. A 200×200 stainless steel mesh (McMaster-Carr, New Brunswick, N.J.) was placed between the stopping screen and the target tissue.

Seven days after gene delivery, target tissue pieces were transferred from the high osmotic medium to selection media. For selection using the BAR gene, CG00526 target tissue pieces were placed onto maintenance medium containing 100 mg/L glufosinate ammonium (Basta®) while those of CG00714 were selected using 20 mg/L bialaphos (Herbiace®). All amino acids were removed from the selection media. After 5 to 8 weeks on these high level selection media, any growing callus from CG00526 was subcultured to media containing 20 mg/L Basta® and growing callus of CG00714 was subcultured to 3 mg/L Basta®.

For selection using the Mannose Phosphate Isomerase gene, both CG00526 and CG00714 target tissues were placed their respective maintenance media containing no sucrose and 1% mannose. The amino acids were not removed from these media. After 5 to 8 weeks, growing callus of CG00526 was subcultured to its maintenance medium containing no sucrose and 1.5% mannose and callus of CG00714 was subcultured to its maintenance medium containing 1% sucrose and 0.5% mannose. Embryogenic callus growing on selection media was subcultured every 2 weeks for 4 to 8 weeks until enough callus was produced to generate 10–20 plants. Tissue surviving selection from an original target tissue piece was subcultured as a single colony and designated as an independent transformation event.

At that point, colonies selected on Basta® were transferred to a modified MS medium (Murashige and Skoog, Physiol. Plant, 15:473–497, 1962) containing 3% sucrose (MS3S) with no selection agent and placed in the light. For CG00526, 0.25mg/L ancymidol and 0.5 mg/L kinetin were added to this medium to induce embryo germination while for CG00714, 2 mg/L benzyl adenine was added. CG00526 colonies selected using mannose were transferred onto a modified MS medium containing 2% sucrose and 1% mannose (MS2S+1M) with the ancymidol and kinetin additions described above. CG00714 colonies selected using mannose were transferred onto a modified MS medium containing 2% sucrose and 0.5% mannose (MS2S+0.5M) with the benzyl adenine addition described above.

Regenerating colonies from Basta® selection were transferred to MS3S media without ancymidol and kinetin or benzyl adenine after 2 weeks. Regenerating colonies of CG00526 and CG00714 from mannose selection were transferred to MS2S+1M and MS2S+0.5M media respectively without hormones after 2 weeks. Regenerating shoots with or without roots from all colonies were transferred to Magenta boxes containing MS3S medium and small plants with roots were eventually recovered and transferred to soil in the greenhouse.

Plants could be tested for expression of the PMI gene using a modified 48-well chlorophenol red assay where the media contains no sucrose and 0.5% mannose. Leaf samples (~5 mm×5 mm) are placed on this assay media and grown in the dark for ~72 hours. If the plant is expressing the PMI gene, it can metabolize the mannose and the media will turn yellow. If not, the media will remain red.

Figure 7:
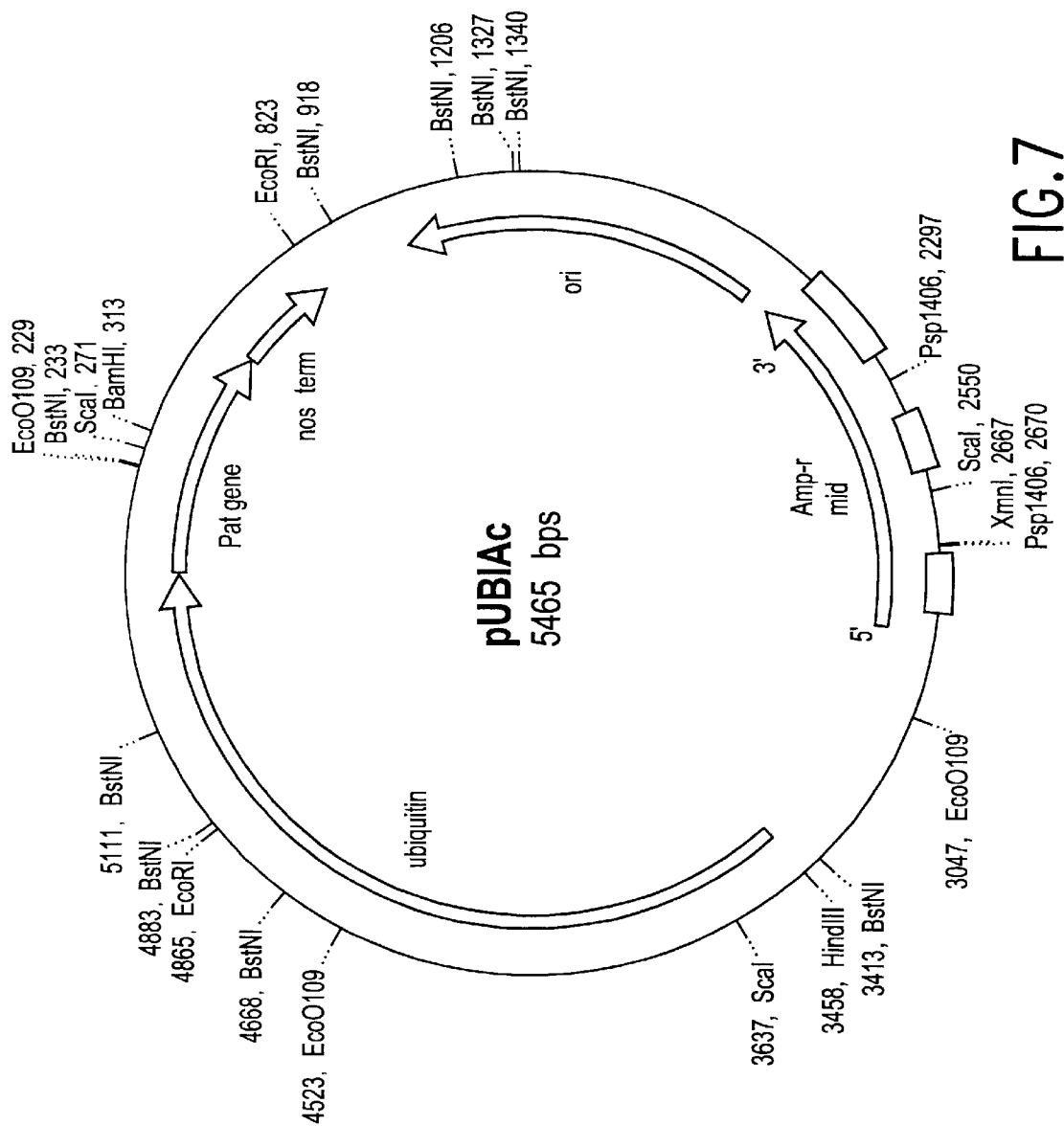
FIG. 7: Map of selectable marker plasmid pUBIAc comprising the pat gene fused to the ubiquitin promoter.

Transformation events have also been created using Type I callus obtained from immature zygotic embryos using standard culture techniques. For gene delivery, approximately 300 mg of the Type I callus was prepared by subculturing to fresh media 1 to 2 days prior to gene delivery, selecting target tissue pieces and placing them in a ring pattern 10 mm from the center of the target plate on medium again containing 12% sucrose. After approximately 4 hours, the tissue was bombarded using the PDS-1000/He Biolistic device from DuPont. The plasmids pCIB5520 and pUBIAc (FIG. 7) were precipitated onto 1 um gold particles using the standard protocol from DuPont. Genes were delivered using two shots per target plate at 650 psi. Approximately 16 hours after gene delivery the callus was transferred to standard culture medium containing 2% sucrose with no selection agent. At 12 or 13 days after gene delivery, target tissue pieces were transferred to selection media containing 40 mg/l phosphinothricin as either Basta or bialaphos. The callus was subcultured on selection for 12 to 16 weeks, after which surviving and growing callus was transferred to standard regeneration medium containing 3 mg/l phosphinothricin as Basta for the production of plants.

Multiple transgenic maize events are produced according to the above procedures, and when tested according to the procedures in Example 3, are shown to be insecticidal. Representative data is set forth in the table below.

Insecticidal Activity of Transgenic Maize Containing hyFLIB

| Event No. | Transforming Plasmid | Activity against European Corn Borer | Activity Against Corn Ear Worm |
|---|---|---|---|
| 601 | pCIB5520, pUBIAc | + | − |
| 602 | pCIB5520, pUBIAc | + | Not tested |
| 605 | pCIB5520, pCIB4784 pUBIAc | + | Not tested |

Additional transformation events are created using the above procedures with the hyFLIB gene and are described below.

Figure 6:
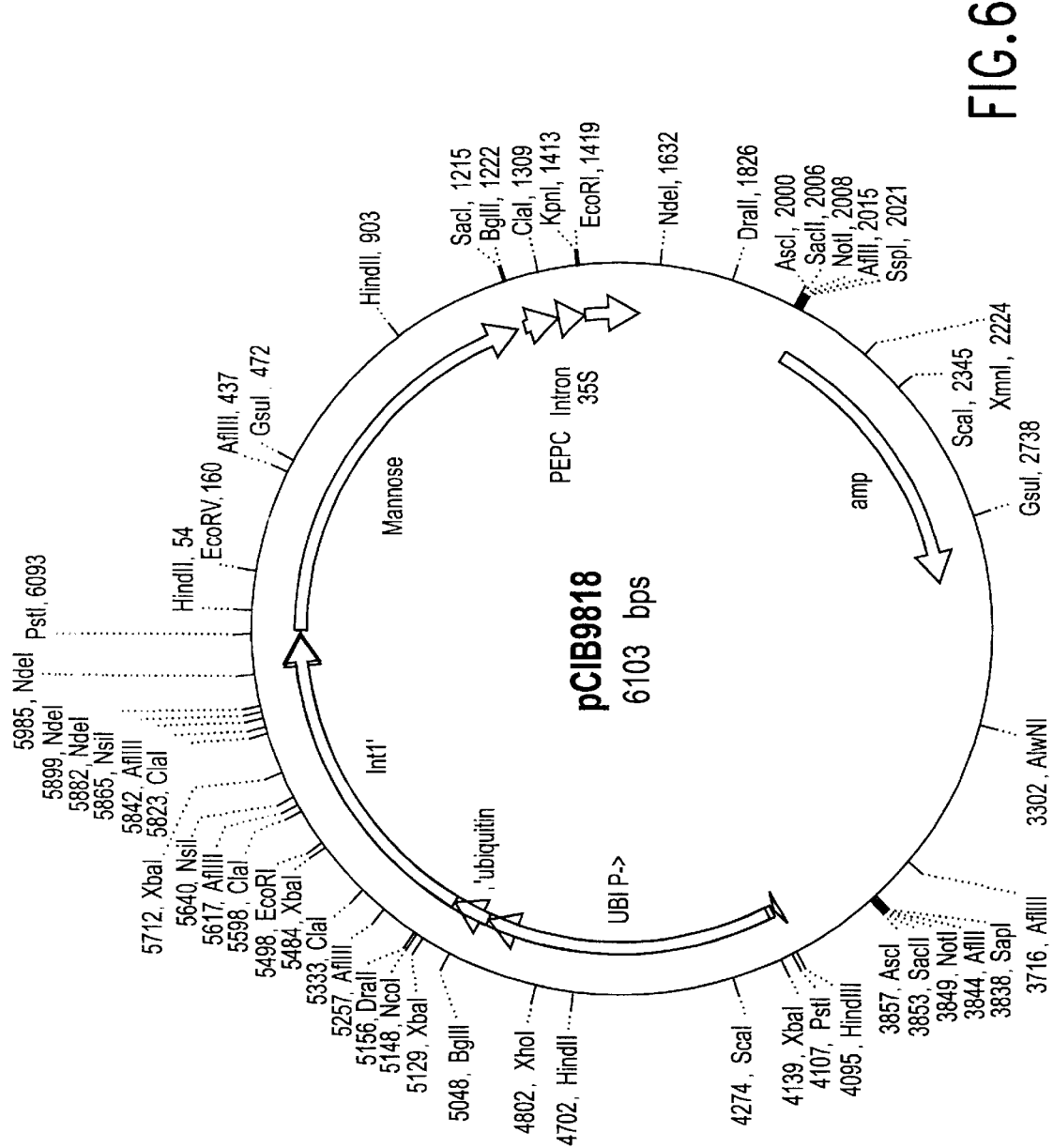
FIG. 6: Map of selectable marker plasmid pCIB9818 comprising the mannose phosphate isomerase (PMI) gene fused to the ubiquitin promoter.

I. HyFLIB events made using the transforming plasmids pCIB9830, pCIB9831, the Selectable Marker Plasmid pCIB9818 (FIG. 6; ubi-MPI) and transformed into genotype CG00714:

1997, 2048, 2057, 2058, 2072, 2108, 2154, 2218, 2191, 2208

II. HyFLIB events containing the transforming plasmids pCIB9830, pCIB9831; the selectable marker plasmid pCIB9818 (ubi-MPI); transformed into genotype CG00526:

2004, 2017, 2018, 2019, 2020, 2021, 2022, 2023, 2024, 2035, 2036, 2041, 2043, 2046,2047, 2059,2071,2119, 2139, 2183,2186

Figure 5:
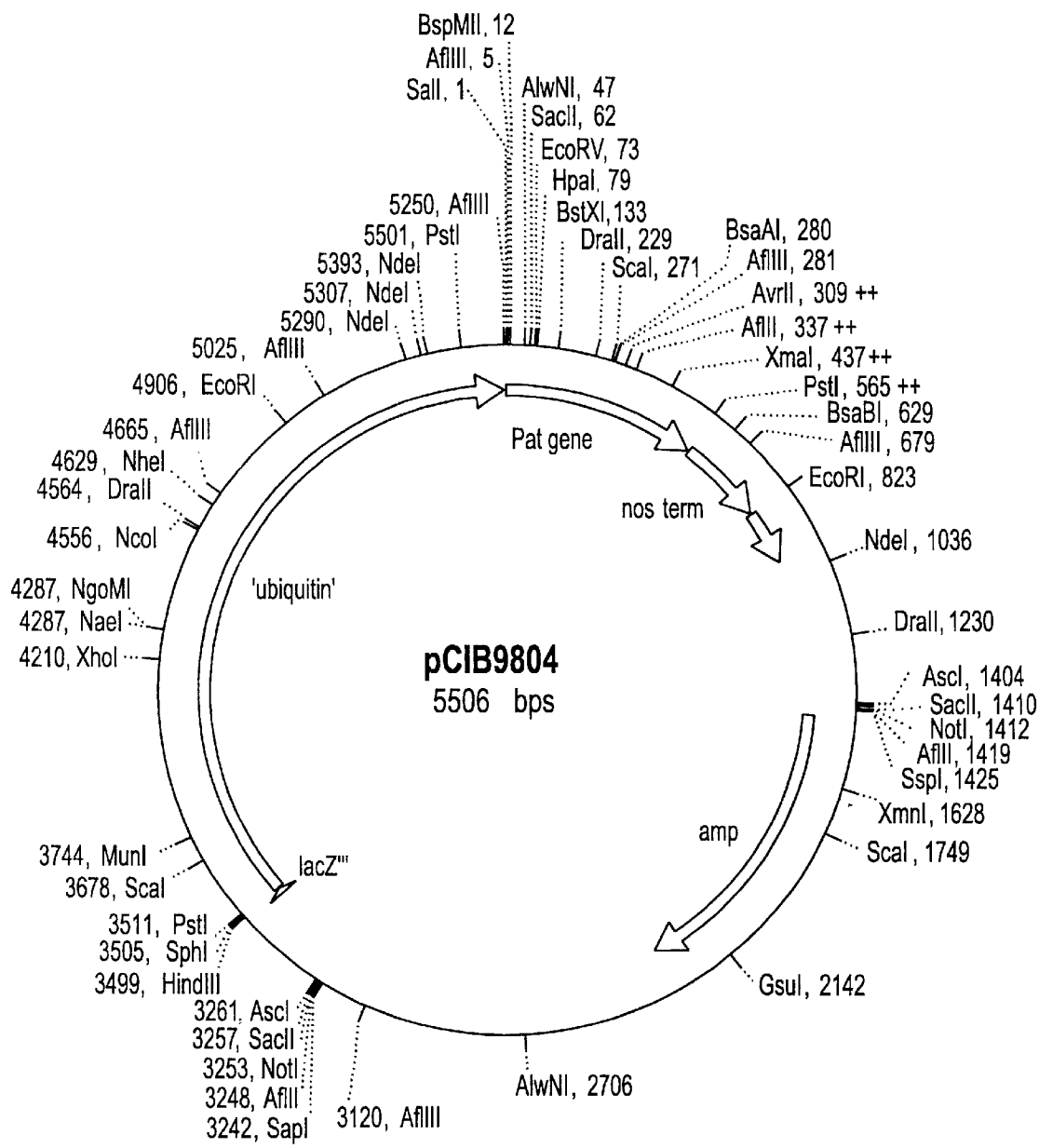
FIG. 5: Map of selectable marker plasmid pCIB9804 comprising the pat gene fused to the ubiquitin promoter.

III. HyFLIB Events Containing the Transforming Plasmids pCIB9830, pCIB9831; the Selectable Marker Plasmid pCIB9804 (FIG. 5; ubi-PAT); Transformed into Genotype CG00714

2009, 2011, 2027, 2028, 2029, 2051, 2090, 2107, 2109, 2113, 2115, 2189

We claim:

1. An isolated DNA molecule comprising a nucleotide sequence encoding a chimeric insecticidal protein of 1200 to 1300 amino acids, wherein said insecticidal protein comprises a cryIB core N-terminal toxin portion of 600 to 1000 amino acids and a cryIA(b) C-terminal protoxin portion of 300 to 600 amino acids, and wherein said nucleotide sequence is set forth in SEQ ID NO:1.

2. An isolated DNA molecule according to claim 1, wherein said nucleotide sequence encodes a chimeric insecticidal protein of 1227 amino acids, wherein said insecticidal protein comprises a cryIB core N-terminal toxin portion of 845 amino acids and a cryIA(b) C-terminal protoxin portion of 382 amino acids.

3. An isolated nucleic acid molecule comprising a nucteotide sequence that encodes a chimeric insecticidal protein, wherein said protein comprises the amino acid sequence set forth in SEQ ID NO:2.

4. An isolated nucleic acid molecule according to claim 3, wherein said nucleotide sequence is a synthetic sequence that has been designed for optimum expression in a plant.

5. An isolated nucleic acid molecule according to claim 4, wherein the plant is a maize plant.

6. An isolated nucleic acid molecule according to claim 3, wherein said nucleotide sequence comprises SEQ ID NO:1.

7. A chimeric gene comprising a promoter operably linked to a coding sequence, wherein said coding sequence is set forth in SEQ ID NO:1.

8. The chimeric gene of claim 7 wherein said promoter is selected from the group consisting of a PEPC promoter, pith promoter, MTL promoter, and ubiquitin promoter.

9. A chimeric gene comprising a promoter sequence operatively linked to the nucleic acid molecule of claim 3.

10. A chimeric gene comprising a promoter sequence operatively linked to the nucleic acid molecule of claim 6.

11. A recombinant vector comprising the chimeric gene of claim 9.

12. A recombinant vector comprising the chimeric gene of claim 10.

13. A plant stably transformed with the chimeric gene of claim 7.

14. A recombinant bacterial or plant host transformed to express a chimeric insecticidal protein comprising a cryIB core N-terminal toxin portion and a cryIA(b) C-terminal protoxin portion, wherein said protein comprises the amino acid sequence set forth in SEQ ID NO:2.

15. A transgenic host cell comprising the chimeric gene of claim 11.

16. A transgenic host cell comprising the chimeric gene of claim 12.

17. A transgenic plant comprising the transgenic host cell of claim 15.

18. A transgenic plant comprising the transgenic host cell of claim 16.

19. A transgenic plant according to claim 17, wherein said plant is selected from the group consisting of maize, sorghum, wheat, sunflower, tomato, cole crops, cotton, rice, soybean, sugarbeet, sugarcane, tobacco, barley, and oilseed rape.

20. A transgenic plant according to claim 18, wherein said plant is selected from the group consisting of maize, sorghum, wheat, sunflower, tomato, cole crops, cotton, rice, soybean, sugarbeet, sugarcane, tobacco, barley, and oilseed rape.

21. A transgenic plant according to claim 19, wherein said plant is a maize plant.

22. A transgenic plant according to claim 20, wherein said plant is a maize plant.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 8854 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: CDS
      (B) LOCATION: 11..3694
      (D) OTHER INFORMATION: /product= "hyFLIB protein"

(ix) FEATURE:
      (A) NAME/KEY: misc_feature
      (B) LOCATION: 8854
      (D) OTHER INFORMATION: /note= "Sequence of pCIB5520 containing coding sequence for hyFLIB protein"

(xi) SEQUENCE DESCRIPTION: SEQ ID NO:1:

```
GGATCCAACA ATG ACC AGC AAC CGC AAG AAC GAG AAC GAG ATC ATC AAC        49
           Met Thr Ser Asn Arg Lys Asn Glu Asn Glu Ile Ile Asn
            1               5                  10

GCC GTG AGC AAC CAC AGC GCC CAG ATG GAC CTG CTG CCC GAC GCC CGC        97
Ala Val Ser Asn His Ser Ala Gln Met Asp Leu Leu Pro Asp Ala Arg
    15                  20                  25

ATC GAG GAC AGC CTG TGC ATC GCC GAG GGC AAC AAC ATC GAC CCC TTC       145
Ile Glu Asp Ser Leu Cys Ile Ala Glu Gly Asn Asn Ile Asp Pro Phe
 30                  35                  40                  45
```

-continued

```
GTG AGC GCC AGC ACC GTG CAG ACC GGC ATC AAC ATC GCC GGC CGC ATC       193
Val Ser Ala Ser Thr Val Gln Thr Gly Ile Asn Ile Ala Gly Arg Ile
            50                  55                  60

CTG GGC GTG CTG GGC GTG CCC TTC GCC GGC CAG CTG GCT AGC TTC TAC       241
Leu Gly Val Leu Gly Val Pro Phe Ala Gly Gln Leu Ala Ser Phe Tyr
                65                  70                  75

AGC TTC CTG GTG GGC GAG CTG TGG CCC CGC GGC CGC GAC CAG TGG GAA       289
Ser Phe Leu Val Gly Glu Leu Trp Pro Arg Gly Arg Asp Gln Trp Glu
                    80                  85                  90

ATC TTC CTG GAG CAC GTG GAG CAG CTG ATC AAC CAG CAG ATC ACC GAG       337
Ile Phe Leu Glu His Val Glu Gln Leu Ile Asn Gln Gln Ile Thr Glu
                        95                 100                 105

AAC GCC CGC AAC ACC GCT CTT GCC CGC CTG CAG GGT CTG GGC GAC AGC       385
Asn Ala Arg Asn Thr Ala Leu Ala Arg Leu Gln Gly Leu Gly Asp Ser
110                 115                 120                 125

TTC CGC GCC TAC CAG CAG AGC CTG GAG GAC TGG CTG GAG AAC CGC GAC       433
Phe Arg Ala Tyr Gln Gln Ser Leu Glu Asp Trp Leu Glu Asn Arg Asp
                130                 135                 140

GAC GCC CGC ACC CGC AGC GTG CTG TAC ACC CAG TAC ATC GCC CTG GAG       481
Asp Ala Arg Thr Arg Ser Val Leu Tyr Thr Gln Tyr Ile Ala Leu Glu
                145                 150                 155

CTG GAC TTC CTG AAC GCC ATG CCC CTG TTC GCC ATT CGA AAC CAG GAG       529
Leu Asp Phe Leu Asn Ala Met Pro Leu Phe Ala Ile Arg Asn Gln Glu
                160                 165                 170

GTG CCC CTG CTG ATG GTG TAC GCC CAG GCC GCC AAC CTG CAC CTG CTG       577
Val Pro Leu Leu Met Val Tyr Ala Gln Ala Ala Asn Leu His Leu Leu
                175                 180                 185

CTG CTG CGC GAC GCC AGC CTG TTC GGC AGC GAG TTC GGC CTG ACC AGC       625
Leu Leu Arg Asp Ala Ser Leu Phe Gly Ser Glu Phe Gly Leu Thr Ser
190                 195                 200                 205

CAG GAG ATC CAG CGC TAC TAC GAG CGC CAG GTG GAG CGC ACC CGC GAC       673
Gln Glu Ile Gln Arg Tyr Tyr Glu Arg Gln Val Glu Arg Thr Arg Asp
                210                 215                 220

TAC AGC GAC TAC TGC GTG GAG TGG TAC AAC ACC GGC CTG AAC AGC TTA       721
Tyr Ser Asp Tyr Cys Val Glu Trp Tyr Asn Thr Gly Leu Asn Ser Leu
                225                 230                 235

AGG GGC ACC AAC GCC GCC AGC TGG GTG CGC TAC AAC CAG TTC CGC CGC       769
Arg Gly Thr Asn Ala Ala Ser Trp Val Arg Tyr Asn Gln Phe Arg Arg
                240                 245                 250

GAC CTG ACC CTG GGC GTG CTG GAC CTG GTG GCC CTG TTC CCC AGC TAC       817
Asp Leu Thr Leu Gly Val Leu Asp Leu Val Ala Leu Phe Pro Ser Tyr
                255                 260                 265

GAC ACC CGC ACC TAC CCC ATC AAC ACC AGC GCC CAG CTG ACC CGC GAG       865
Asp Thr Arg Thr Tyr Pro Ile Asn Thr Ser Ala Gln Leu Thr Arg Glu
270                 275                 280                 285

GTG TAC ACC GAC GCC ATC GGC GCC ACC GGC GTG AAC ATG GCC AGC ATG       913
Val Tyr Thr Asp Ala Ile Gly Ala Thr Gly Val Asn Met Ala Ser Met
                290                 295                 300

AAC TGG TAC AAC AAC AAC GCC CCC AGC TTC AGC GCC ATC GAG GCC GCC       961
Asn Trp Tyr Asn Asn Asn Ala Pro Ser Phe Ser Ala Ile Glu Ala Ala
                305                 310                 315

GCC ATC CGC AGC CCC CAC CTG CTG GAC TTC CTG GAG CAG CTG ACC ATC      1009
Ala Ile Arg Ser Pro His Leu Leu Asp Phe Leu Glu Gln Leu Thr Ile
                320                 325                 330

TTC AGC GCC AGC AGC CGC TGG AGC AAC ACC CGC CAC ATG ACC TAC TGG      1057
Phe Ser Ala Ser Ser Arg Trp Ser Asn Thr Arg His Met Thr Tyr Trp
                335                 340                 345

CGC GGC CAC ACC ATC CAG TCT AGA CCC ATC GGC GGC GGC CTG AAC ACC      1105
Arg Gly His Thr Ile Gln Ser Arg Pro Ile Gly Gly Gly Leu Asn Thr
```

```
                                                           -continued
350                  355                  360                  365
AGC ACC CAC GGC GCC ACC AAC ACC ACC ATC AAC CCC GTG ACC CTG CGC    1153
Ser Thr His Gly Ala Thr Asn Thr Thr Ile Asn Pro Val Thr Leu Arg
                370                  375                  380

TTC GCC TCC CGA GAC GTC TAC CGC ACC GAG AGC TAC GCC GGC GTG CTG    1201
Phe Ala Ser Arg Asp Val Tyr Arg Thr Glu Ser Tyr Ala Gly Val Leu
                385                  390                  395

CTG TGG GGC ATC TAC CTG GAG CCC ATC CAC GGC GTG CCC ACC GTG CGC    1249
Leu Trp Gly Ile Tyr Leu Glu Pro Ile His Gly Val Pro Thr Val Arg
            400                  405                  410

TTC AAC TTC ACC AAC CCC CAG AAC ATC AGC GAC CGC GGC ACC GCC AAC    1297
Phe Asn Phe Thr Asn Pro Gln Asn Ile Ser Asp Arg Gly Thr Ala Asn
            415                  420                  425

TAC AGC CAG CCC TAC GAG AGC CCC GGG TTG CAG CTG AAG GAC AGC GAG    1345
Tyr Ser Gln Pro Tyr Glu Ser Pro Gly Leu Gln Leu Lys Asp Ser Glu
430                  435                  440                  445

ACC GAG CTG CCC CCC GAG ACC ACC GAG CGC CCC AAC TAC GAG AGC TAC    1393
Thr Glu Leu Pro Pro Glu Thr Thr Glu Arg Pro Asn Tyr Glu Ser Tyr
                450                  455                  460

AGC CAC CGC CTG AGC CAC ATC GGC ATC ATC TTG CAG AGC CGC GTG AAC    1441
Ser His Arg Leu Ser His Ile Gly Ile Ile Leu Gln Ser Arg Val Asn
                465                  470                  475

GTG CCC GTG TAC AGC TGG ACC CAC CGC AGC GCC GAC CGC ACC AAC ACC    1489
Val Pro Val Tyr Ser Trp Thr His Arg Ser Ala Asp Arg Thr Asn Thr
            480                  485                  490

ATC GGC CCC AAC CGC ATC ACC CAG ATC CCC ATG GTG AAG GCC AGC GAG    1537
Ile Gly Pro Asn Arg Ile Thr Gln Ile Pro Met Val Lys Ala Ser Glu
495                  500                  505

CTG CCC CAG GGC ACC ACC GTG GTG CGC GGC CCC GGC TTC ACC GGC GGC    1585
Leu Pro Gln Gly Thr Thr Val Val Arg Gly Pro Gly Phe Thr Gly Gly
510                  515                  520                  525

GAC ATC CTG CGC CGC ACC AAC ACC GGC GGC TTC GGC CCC ATC CGC GTG    1633
Asp Ile Leu Arg Arg Thr Asn Thr Gly Gly Phe Gly Pro Ile Arg Val
                530                  535                  540

ACC GTG AAC GGC CCC CTG ACC CAG CGC TAC CGC ATC GGC TTC CGC TAC    1681
Thr Val Asn Gly Pro Leu Thr Gln Arg Tyr Arg Ile Gly Phe Arg Tyr
            545                  550                  555

GCC AGC ACC GTG GAC TTC GAC TTC TTC GTG AGC CGC GGC GGC ACC ACC    1729
Ala Ser Thr Val Asp Phe Asp Phe Phe Val Ser Arg Gly Gly Thr Thr
            560                  565                  570

GTG AAC AAC TTC CGC TTC CTG CGC ACC ATG AAC AGC GGC GAC GAG CTG    1777
Val Asn Asn Phe Arg Phe Leu Arg Thr Met Asn Ser Gly Asp Glu Leu
            575                  580                  585

AAG TAC GGC AAC TTC GTG CGC CGC GCC TTC ACC ACC CCC TTC ACC TTC    1825
Lys Tyr Gly Asn Phe Val Arg Arg Ala Phe Thr Thr Pro Phe Thr Phe
590                  595                  600                  605

ACC CAG ATC CAG AAC ATC ATC CGC ACC AGC ATC CAG GGC CTG AGC GGC    1873
Thr Gln Ile Gln Asn Ile Ile Arg Thr Ser Ile Gln Gly Leu Ser Gly
                610                  615                  620

AAC GGC GAG GTG TAC ATC GAC AAG ATC GAG ATC ATC CCC GTG ACT GCC    1921
Asn Gly Glu Val Tyr Ile Asp Lys Ile Glu Ile Ile Pro Val Thr Ala
                625                  630                  635

ACC TTC GAG GCC GAG TAT GAC CTG GAG CGC GCC CAG GAG GCC GTG AAC    1969
Thr Phe Glu Ala Glu Tyr Asp Leu Glu Arg Ala Gln Glu Ala Val Asn
            640                  645                  650

GCC CTG TTC ACC AAC ACC AAC CCC CGC CGC CTG AAG ACC GAC GTG ACC    2017
Ala Leu Phe Thr Asn Thr Asn Pro Arg Arg Leu Lys Thr Asp Val Thr
            655                  660                  665

AAC TAC CAC ATC GAC CAG GTG AGC AAC CTG GTG GCC TGC CTG AGC GAC    2065
```

```
Asn Tyr His Ile Asp Gln Val Ser Asn Leu Val Ala Cys Leu Ser Asp
670             675             680             685

GCA TTC TGC CTG GAC GAG AAG CGC GAG CTG CTG GAG AAG GTG AAG TAC      2113
Ala Phe Cys Leu Asp Glu Lys Arg Glu Leu Leu Glu Lys Val Lys Tyr
            690             695             700

GCC AAG CGC CTG AGC GAC GAG CGC AAC CTG CTT CAG GAC CCC AAC TTC      2161
Ala Lys Arg Leu Ser Asp Glu Arg Asn Leu Leu Gln Asp Pro Asn Phe
        705             710             715

ACC AGC ATC AAC AAG CAG CCC GAC TTC ATC AGC ACC AAC GAG CAG AGC      2209
Thr Ser Ile Asn Lys Gln Pro Asp Phe Ile Ser Thr Asn Glu Gln Ser
    720             725             730

AAC TTC ACC AGC ATC CAC GAG CAG AGC GAG CAC GGC TGG TGG GGC AGC      2257
Asn Phe Thr Ser Ile His Glu Gln Ser Glu His Gly Trp Trp Gly Ser
735             740             745

GAG AAC ATC ACC ATC CAG GAG GGC AAC GAC GTG TTC AAG GAG AAC TAC      2305
Glu Asn Ile Thr Ile Gln Glu Gly Asn Asp Val Phe Lys Glu Asn Tyr
750             755             760             765

GTG ACC CTG CCC GGT ACC TTC AAC GAG TGC TAC CCC ACC TAC CTG TAC      2353
Val Thr Leu Pro Gly Thr Phe Asn Glu Cys Tyr Pro Thr Tyr Leu Tyr
            770             775             780

CAG AAG ATC GGC GAG AGC GAG CTG AAG GCC TAC ACC CGC TAC CAG CTG      2401
Gln Lys Ile Gly Glu Ser Glu Leu Lys Ala Tyr Thr Arg Tyr Gln Leu
        785             790             795

CGC GGC TAC ATC GAG GAC AGC CAG GAC CTG GAG ATA TAC CTG ATC CGC      2449
Arg Gly Tyr Ile Glu Asp Ser Gln Asp Leu Glu Ile Tyr Leu Ile Arg
    800             805             810

TAC AAC GCC AAG CAC GAG ACC CTG GAC GTG CCC GGC ACC GAG AGC CTG      2497
Tyr Asn Ala Lys His Glu Thr Leu Asp Val Pro Gly Thr Glu Ser Leu
815             820             825

TGG CCC CTG AGC GTG GAG AGC CCC ATC GGC CGC TGC GGC GAG CCC AAT      2545
Trp Pro Leu Ser Val Glu Ser Pro Ile Gly Arg Cys Gly Glu Pro Asn
830             835             840             845

CGA TGC GCT CCG CAC CTG GAG TGG AAC CCG GAC CTA GAC TGC AGC TGC      2593
Arg Cys Ala Pro His Leu Glu Trp Asn Pro Asp Leu Asp Cys Ser Cys
            850             855             860

AGG GAC GGG GAG AAG TGC GCC CAC CAC AGC CAC CAC TTC AGC CTG GAC      2641
Arg Asp Gly Glu Lys Cys Ala His His Ser His His Phe Ser Leu Asp
        865             870             875

ATC GAC GTG GGC TGC ACC GAC CTG AAC GAG GAC CTG GGC GTG TGG GTG      2689
Ile Asp Val Gly Cys Thr Asp Leu Asn Glu Asp Leu Gly Val Trp Val
    880             885             890

ATC TTC AAG ATC AAG ACC CAG GAC GGC CAC GCC CGC CTG GGC AAT CTA      2737
Ile Phe Lys Ile Lys Thr Gln Asp Gly His Ala Arg Leu Gly Asn Leu
895             900             905

GAG TTC CTG GAG GAG AAG CCC CTG GTG GGC GAG GCC CTG GCC CGC GTG      2785
Glu Phe Leu Glu Glu Lys Pro Leu Val Gly Glu Ala Leu Ala Arg Val
910             915             920             925

AAG CGC GCC GAG AAG AAG TGG CGC GAC AAG CGC GAG AAG CTG GAG TGG      2833
Lys Arg Ala Glu Lys Lys Trp Arg Asp Lys Arg Glu Lys Leu Glu Trp
            930             935             940

GAG ACC AAC ATC GTG TAC AAG GAG GCC AAG GAG AGC GTG GAC GCC CTG      2881
Glu Thr Asn Ile Val Tyr Lys Glu Ala Lys Glu Ser Val Asp Ala Leu
        945             950             955

TTC GTG AAC AGC CAG TAC GAC CGC CTG CAG GCC GAC ACC AAC ATC GCC      2929
Phe Val Asn Ser Gln Tyr Asp Arg Leu Gln Ala Asp Thr Asn Ile Ala
    960             965             970

ATG ATC CAC GCC GCC GAC AAG CGC GTG CAC AGC ATT CGC GAG GCC TAC      2977
Met Ile His Ala Ala Asp Lys Arg Val His Ser Ile Arg Glu Ala Tyr
975             980             985
```

```
CTG CCC GAG CTG AGC GTG ATC CCC GGC GTG AAC GCC GCC ATC TTC GAG       3025
Leu Pro Glu Leu Ser Val Ile Pro Gly Val Asn Ala Ala Ile Phe Glu
990             995              1000            1005

GAA CTC GAG GGC CGC ATC TTC ACC GCC TTC AGC CTG TAC GAC GCC CGC       3073
Glu Leu Glu Gly Arg Ile Phe Thr Ala Phe Ser Leu Tyr Asp Ala Arg
        1010            1015            1020

AAC GTG ATC AAG AAC GGC GAC TTC AAC AAC GGC CTG AGC TGC TGG AAC       3121
Asn Val Ile Lys Asn Gly Asp Phe Asn Asn Gly Leu Ser Cys Trp Asn
            1025            1030            1035

GTG AAG GGC CAC GTG GAC GTG GAG GAG CAG AAC AAC CAC CGC AGC GTG       3169
Val Lys Gly His Val Asp Val Glu Glu Gln Asn Asn His Arg Ser Val
        1040            1045            1050

CTG GTG GTG CCC GAG TGG GAG GCC GAG GTG AGC CAG GAG GTG CGC GTG       3217
Leu Val Val Pro Glu Trp Glu Ala Glu Val Ser Gln Glu Val Arg Val
            1055            1060            1065

TGC CCC GGC CGC GGC TAC ATC CTG CGC GTG ACC GCC TAC AAG GAG GGC       3265
Cys Pro Gly Arg Gly Tyr Ile Leu Arg Val Thr Ala Tyr Lys Glu Gly
1070            1075            1080            1085

TAC GGC GAG GGC TGC GTG ACC ATC CAC GAG ATC GAG AAC AAC ACC GAC       3313
Tyr Gly Glu Gly Cys Val Thr Ile His Glu Ile Glu Asn Asn Thr Asp
            1090            1095            1100

GAG CTC AAG TTC AGC AAC TGC GTG GAG GAG GAG GTT TAC CCC AAC AAC       3361
Glu Leu Lys Phe Ser Asn Cys Val Glu Glu Glu Val Tyr Pro Asn Asn
            1105            1110            1115

ACC GTG ACC TGC AAC GAC TAC ACC GCG ACC CAG GAG GAG TAC GAA GGC       3409
Thr Val Thr Cys Asn Asp Tyr Thr Ala Thr Gln Glu Glu Tyr Glu Gly
            1120            1125            1130

ACC TAC ACC TCT CGC AAC AGG GGT TAC GAC GGC GCC TAC GAG TCC AAC       3457
Thr Tyr Thr Ser Arg Asn Arg Gly Tyr Asp Gly Ala Tyr Glu Ser Asn
            1135            1140            1145

AGC TCC GTG CCA GCC GAC TAC GCC AGC GCC TAC GAG GAG AAA GCC TAC       3505
Ser Ser Val Pro Ala Asp Tyr Ala Ser Ala Tyr Glu Glu Lys Ala Tyr
1150            1155            1160            1165

ACC GAC GGT AGA CGC GAC AAC CCA TGT GAG AGC AAC AGA GGC TAC GGC       3553
Thr Asp Gly Arg Arg Asp Asn Pro Cys Glu Ser Asn Arg Gly Tyr Gly
            1170            1175            1180

GAC TAC ACC CCC CTG CCC GCT GGA TAC GTG ACC AAG GAG CTG GAG TAC       3601
Asp Tyr Thr Pro Leu Pro Ala Gly Tyr Val Thr Lys Glu Leu Glu Tyr
            1185            1190            1195

TTC CCC GAG ACC GAC AAG GTG TGG ATC GAG ATT GGC GAG ACC GAG GGC       3649
Phe Pro Glu Thr Asp Lys Val Trp Ile Glu Ile Gly Glu Thr Glu Gly
            1200            1205            1210

ACC TTC ATC GTG GAC AGC GTG GAG CTG CTG CTG ATG GAG GAG TAG           3694
Thr Phe Ile Val Asp Ser Val Glu Leu Leu Leu Met Glu Glu *
            1215            1220            1225

TAGATCTGTT GTACAAAAAC CAGCAACTCA CTGCACTGCA CTTCACTTCA CTTCACTGTA     3754

TGAATAAAAG TCTGGTGTCT GGTTCCTGAT CGATGACTGA CTACTCCACT TTGTGCAGAA     3814

CTTAGTATGT ATTTGTATTT GTAAAATACT TCTATCAATA AAATTTCTAA TTCCTAAAAC     3874

CAAAATCCAG TGGGTACCGA ATTCACTGGC CGTCGTTTTA CAACGTCGTG ACTGGGAAAA     3934

CCCTGGCGTT ACCCAACTTA ATCGCCTTGC AGCACATCCC CCTTTCGCCA GCTGGCGTAA     3994

TAGCGAAGAG GCCCGCACCG ATCGCCCTTC CCAACAGTTG CGCAGCCTGA ATGGCGAATG     4054

GCGCCTGATG CGGTATTTTC TCCTTACGCA TCTGTGCGGT ATTTCACACC GCATATGGTG     4114

CACTCTCAGT ACAATCTGCT CTGATGCCGC ATAGTTAAGC CAGCCCCGAC ACCCGCCAAC     4174

ACCCGCTGAC GCGCCCTGAC GGGCTTGTCT GCTCCCGGCA TCCGCTTACA GACAAGCTGT     4234

GACCGTCTCC GGGAGCTGCA TGTGTCAGAG GTTTTCACCG TCATCACCGA AACGCGCGAG     4294
```

```
ACGAAAGGGC CTCGTGATAC GCCTATTTTT ATAGGTTAAT GTCATGATAA TAATGGTTTC    4354

TTAGACGTCA GGTGGCACTT TTCGGGGAAA TGTGCGCGGA ACCCCTATTT GTTTATTTTT    4414

CTAAATACAT TCAAATATGT ATCCGCTCAT GAGACAATAA CCCTGATAAA TGCTTCAATA    4474

ATATTGAAAA AGGAAGAGTA TGAGTATTCA ACATTTCCGT GTCGCCCTTA TTCCCTTTTT    4534

TGCGGCATTT TGCCTTCCTG TTTTTGCTCA CCCAGAAACG CTGGTGAAAG TAAAAGATGC    4594

TGAAGATCAG TTGGGTGCAC GAGTGGGTTA CATCGAACTG GATCTCAACA GCGGTAAGAT    4654

CCTTGAGAGT TTTCGCCCCG AAGAACGTTT TCCAATGATG AGCACTTTTA AAGTTCTGCT    4714

ATGTGGCGCG GTATTATCCC GTATTGACGC CGGGCAAGAG CAACTCGGTC GCCGCATACA    4774

CTATTCTCAG AATGACTTGG TTGAGTACTC ACCAGTCACA GAAAAGCATC TTACGGATGG    4834

CATGACAGTA AGAGAATTAT GCAGTGCTGC CATAACCATG AGTGATAACA CTGCGGCCAA    4894

CTTACTTCTG ACAACGATCG GAGGACCGAA GGAGCTAACC GCTTTTTTGC ACAACATGGG    4954

GGATCATGTA ACTCGCCTTG ATCGTTGGGA ACCGGAGCTG AATGAAGCCA TACCAAACGA    5014

CGAGCGTGAC ACCACGATGC CTGTAGCAAT GGCAACAACG TTGCGCAAAC TATTAACTGG    5074

CGAACTACTT ACTCTAGCTT CCCGGCAACA ATTAATAGAC TGGATGGAGG CGGATAAAGT    5134

TGCAGGACCA CTTCTGCGCT CGGCCCTTCC GGCTGGCTGG TTTATTGCTG ATAAATCTGG    5194

AGCCGGTGAG CGTGGGTCTC GCGGTATCAT TGCAGCACTG GGGCCAGATG GTAAGCCCTC    5254

CCGTATCGTA GTTATCTACA CGACGGGGAG TCAGCAACT ATGGATGAAC GAAATAGACA    5314

GATCGCTGAG ATAGGTGCCT CACTGATTAA GCATTGGTAA CTGTCAGACC AAGTTTACTC    5374

ATATATACTT TAGATTGATT TAAAACTTCA TTTTTAATTT AAAAGGATCT AGGTGAAGAT    5434

CCTTTTTGAT AATCTCATGA CCAAAATCCC TTAACGTGAG TTTTCGTTCC ACTGAGCGTC    5494

AGACCCCGTA GAAAAGATCA AAGGATCTTC TTGAGATCCT TTTTTTCTGC GCGTAATCTG    5554

CTGCTTGCAA ACAAAAAAAC CACCGCTACC AGCGGTGGTT TGTTTGCCGG ATCAAGAGCT    5614

ACCAACTCTT TTTCCGAAGG TAACTGGCTT CAGCAGAGCG CAGATACCAA ATACTGTCCT    5674

TCTAGTGTAG CCGTAGTTAG GCCACCACTT CAAGAACTCT GTAGCACCGC CTACATACCT    5734

CGCTCTGCTA ATCCTGTTAC CAGTGGCTGC TGCCAGTGGC GATAAGTCGT GTCTTACCGG    5794

GTTGGACTCA AGACGATAGT TACCGGATAA GGCGCAGCGG TCGGGCTGAA CGGGGGGTTC    5854

GTGCACACAG CCCAGCTTGG AGCGAACGAC CTACACCGAA CTGAGATACC TACAGCGTGA    5914

GCTATGAGAA AGCGCCACGC TTCCCGAAGG GAGAAAGGCG GACAGGTATC CGGTAAGCGG    5974

CAGGGTCGGA ACAGGAGAGC GCACGAGGGA GCTTCCAGGG GGAAACGCCT GGTATCTTTA    6034

TAGTCCTGTC GGGTTTCGCC ACCTCTGACT TGAGCGTCGA TTTTTGTGAT GCTCGTCAGG    6094

GGGGCGGAGC CTATGAAAA ACGCCAGCAA CGCGGCCTTT TTACGGTTCC TGGCCTTTTG    6154

CTGGCCTTTT GCTCACATGT TCTTTCCTGC GTTATCCCCT GATTCTGTGG ATAACCGTAT    6214

TACCGCCTTT GAGTGAGCTG ATACCGCTCG CCGCAGCCGA ACGACCGAGC GCAGCGAGTC    6274

AGTGAGCGAG GAAGCGGAAG AGCGCCCAAT ACGCAAACCG CCTCTCCCCG CGCGTTGGCC    6334

GATTCATTAA TGCAGCTGGC ACGACAGGTT TCCCGACTGG AAAGCGGGCA GTGAGCGCAA    6394

CGCAATTAAT GTGAGTTAGC TCACTCATTA GGCACCCCAG GCTTTACACT TTATGCTTCC    6454

GGCTCGTATG TTGTGTGGAA TTGTGAGCGG ATAACAATTT CACACAGGAA ACAGCTATGA    6514

CCATGATTAC GCCAAGCTTG TGAGGCAACC CAAGATAGGT GAAAGATAAG CTACCTTTGT    6574

CACAATTGAA GATTCGTGCA AGGTGGTTCA ACTATTATTC TGAGATGTTT ATTGGGACCA    6634
```

```
TTGAGGACCT TTGAGTAATT AACTCTCAAC CTTGTGGAAA TTCGTTACCA ACTGGGTTGC    6694

ATAGGATTTC ATGATTAAGA GTGTGTTTGG TTTAGCTGTG AGTTTTCTCC TATGAAAAAA    6754

CTGTTGTGAG AAAAAATAGT TGGAAGTCGT TTAGTTCAAA CTGTTGTGAG TTATCCACTG    6814

TAAACAAATT GTATATTGTT TATATACACT CTGTTTAAAT ATATCTCTTA ATCAGTATAT    6874

ATAATTAAAA AACTAATTTC ACATTTGTGT TCCTAATATT TTTTACAAAT AAATCATTGT    6934

TTAATTCCAT TTGTAATAAG TTTTTATTAA AATTGCTTTT ATTTCATTTA TTATAAACAT    6994

TTAATTGTTT TAATCCTATT TTAGTTTTAA TTTATTGTAT CTATTTATTA ATATAACGAA    7054

CTTCGATAAG AAACAAAAGC AAGGTCAAGG TGTTTTTTCA AAGTAGTTGT GGAAAAGCTG    7114

AACCCCTTTT ATTCACTTTT AGAAGCAGGA AAACAGAACA AACAGACCCT AAAAATGTGT    7174

GAATTTTTAG CAGGTTAATT ATTCGCATCT CTTTGGTCAT GTTTAAGAGG CTGGAATAGA    7234

TCAACTGCAA GAACACATAG CAGAGTGGAT AGGGGGGGGG GGGGGGGGGG AGGGTCGTCG    7294

TCTCCCTATC TGACCTCTCT TCTGCATTGG ATTGCCTTTT TCGGTACTCT ATTTAAAACT    7354

TAAAAGTACA AATGAGGTGC CGGATTGATG GAGTGATATA TAAGTTTGAT GTGTTTTTCA    7414

CATAAGTGAC AAGTATTATT GAAAGAGAAA AAAAAAAACA TTTGCATTGC TACTGTTTGC    7474

ATATGGGAAA ATTGAGAATT GTATCATGCC ATGGCCGATC AGTTCTTTAC TTAGCTCGAT    7534

GTAATGCACA ATGTTGATAG TATGTCGAGG ATCTAGCGAT GTAATGGTGT TAGGACACGT    7594

GGTTAGCTAC TAATATAAAT GTAAGGTCAT TCGATGGTTT TTCTATTTTC AATTACCTAG    7654

CATTATCTCA TTTCTAATTG TGATAACAAA TGCATTAGAC CATAATTCTG TAAATATGTA    7714

CATTTAAGCA CACAGTCTAT ATTTTAAAAT TCTTCTTTTT GTGTGGATAT CCCAACCCAA    7774

ATCCACCTCT CTCTTCAATC CGTGCATGTC ACCGCTGCCA AGTGCCAACA ACACATCGCA    7834

TCGTGCATAT CTTTGTTGGC TTGTGCACGG TCGGCGCCAA TGGAGGAGAC ACCTGTACGG    7894

TGCCCTTGGT AGAACAACAT CCTTATCCCT ATATGTATGG TGCCCTTCGT AGAATGACAC    7954

CCCTTATCCC TACAATAGCC ATGTATGCAT ACCAAGAATT AAATATACTT TTTCTTGAAC    8014

CACAATAATT TATTATAGCG GCACTTCTTG TTCAGGTTGA ACACTTATTT GGAACAATAA    8074

AATGCCGAGT TCCTAACCAC AGGTTCACTT TTTTTTTTCC TTATCCTCCT AGGAAACTAA    8134

ATTTTAAAAT CATAAATTAA TTTAAATGTT AATGGAAACA AAAAATTATC TACAAAGACG    8194

ACTCTTAGCC ACAGCCGCCT CACTGCACCC TCAACCACAT CCTGCAAACA GACACCCTCG    8254

CCACATCCCT CCAGATTCTT CACTCCGATG CAGCCTACTT GCTAACAGAC GCCCTCTCCA    8314

CATCCTGCAA AGCATTCCTC CAAATTCTTG CGATCCCCCG AATCCAGCAT TAACTGCTAA    8374

GGGACGCCCT CTCCACATCC TGCTACCCAA TTAGCCAACG GAATAACACA AGAAGGCAGG    8434

TGAGCAGTGA CAAAGCACGT CAACAGCACC GAGCCAAGCC AAAAAGGAGC AAGGAGGAGC    8494

AAGCCCAAGC CGCAGCCGCA GCTCTCCAGG TCCCCTTGCG ATTGCCGCCA GCAGTAGCAG    8554

ACACCCCTCT CCACATCCCC TCCGGCCGCT AACAGCAGCA AGCCAAGCCA AAAAGGAGCC    8614

TCAGCCGCAG CCGGTTCCGT TGCGGTTACC GCCGATCACA TGCCCAAGGC CGCGCCTTTC    8674

CGAACGCCGA GGGCCGCCCG TTCCCGTGCA CAGCCACACA CACACCCGCC CGCCAACGAC    8734

TCCCCATCCC TATTTGAACC CACCCGCGCA CTGCATTGAT CACCAATCGC ATCGCAGCAG    8794

CACGAGCAGC ACGCCGTGCC GCTCCAACCA TCTCGCTTCC GTGCTTAGCT TCCCGCCGCG    8854
```

(2) INFORMATION FOR SEQ ID NO:2:

(i) SEQUENCE CHARACTERISTICS:
        (A) LENGTH: 1227 amino acids (B) TYPE: amino acid
(D) TOPOLOGY: linear (ii) MOLECULE TYPE: protein (xi) SEQUENCE DESCRIPTION: SEQ ID NO:2:

```
Met Thr Ser Asn Arg Lys Asn Glu Asn Glu Ile Ile Asn Ala Val Ser
 1               5                  10                  15

Asn His Ser Ala Gln Met Asp Leu Leu Pro Asp Ala Arg Ile Glu Asp
                 20                  25                  30

Ser Leu Cys Ile Ala Glu Gly Asn Asn Ile Asp Pro Phe Val Ser Ala
             35                  40                  45

Ser Thr Val Gln Thr Gly Ile Asn Ile Ala Gly Arg Ile Leu Gly Val
     50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                 85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Leu Asn Thr Ser Thr His
        355                 360                 365

Gly Ala Thr Asn Thr Thr Ile Asn Pro Val Thr Leu Arg Phe Ala Ser
370                 375                 380
```

-continued

```
Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
        595                 600                 605

Gln Asn Ile Ile Arg Thr Ser Ile Gln Gly Leu Ser Gly Asn Gly Glu
        610                 615                 620

Val Tyr Ile Asp Lys Ile Glu Ile Ile Pro Val Thr Ala Thr Phe Glu
625                 630                 635                 640

Ala Glu Tyr Asp Leu Glu Arg Ala Gln Glu Ala Val Asn Ala Leu Phe
                645                 650                 655

Thr Asn Thr Asn Pro Arg Arg Leu Lys Thr Asp Val Thr Asn Tyr His
            660                 665                 670

Ile Asp Gln Val Ser Asn Leu Val Ala Cys Leu Ser Asp Ala Phe Cys
        675                 680                 685

Leu Asp Glu Lys Arg Glu Leu Leu Glu Lys Val Lys Tyr Ala Lys Arg
690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
            740                 745                 750

Thr Ile Gln Glu Gly Asn Asp Val Phe Lys Glu Asn Tyr Val Thr Leu
        755                 760                 765

Pro Gly Thr Phe Asn Glu Cys Tyr Pro Thr Tyr Leu Tyr Gln Lys Ile
770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
```

-continued

```
                805                 810                 815
Lys His Glu Thr Leu Asp Val Pro Gly Thr Glu Ser Leu Trp Pro Leu
            820                 825                 830
Ser Val Glu Ser Pro Ile Gly Arg Cys Gly Pro Asn Arg Cys Ala
            835                 840                 845
Pro His Leu Glu Trp Asn Pro Asp Leu Asp Cys Ser Cys Arg Asp Gly
            850                 855                 860
Glu Lys Cys Ala His Ser His His Phe Ser Leu Asp Ile Asp Val
865                 870                 875                 880
Gly Cys Thr Asp Leu Asn Glu Asp Leu Gly Val Trp Val Ile Phe Lys
            885                 890                 895
Ile Lys Thr Gln Asp Gly His Ala Arg Leu Gly Asn Leu Glu Phe Leu
            900                 905                 910
Glu Glu Lys Pro Leu Val Gly Glu Ala Leu Ala Arg Val Lys Arg Ala
            915                 920                 925
Glu Lys Lys Trp Arg Asp Lys Arg Glu Lys Leu Glu Trp Glu Thr Asn
            930                 935                 940
Ile Val Tyr Lys Glu Ala Lys Glu Ser Val Asp Ala Leu Phe Val Asn
945                 950                 955                 960
Ser Gln Tyr Asp Arg Leu Gln Ala Asp Thr Asn Ile Ala Met Ile His
            965                 970                 975
Ala Ala Asp Lys Arg Val His Ser Ile Arg Glu Ala Tyr Leu Pro Glu
            980                 985                 990
Leu Ser Val Ile Pro Gly Val Asn Ala Ala Ile Phe Glu Glu Leu Glu
            995                 1000                1005
Gly Arg Ile Phe Thr Ala Phe Ser Leu Tyr Asp Ala Arg Asn Val Ile
            1010                1015                1020
Lys Asn Gly Asp Phe Asn Asn Gly Leu Ser Cys Trp Asn Val Lys Gly
1025                1030                1035                1040
His Val Asp Val Glu Glu Gln Asn Asn His Arg Ser Val Leu Val Val
            1045                1050                1055
Pro Glu Trp Glu Ala Glu Val Ser Gln Glu Val Arg Val Cys Pro Gly
            1060                1065                1070
Arg Gly Tyr Ile Leu Arg Val Thr Ala Tyr Lys Glu Gly Tyr Gly Glu
            1075                1080                1085
Gly Cys Val Thr Ile His Glu Ile Glu Asn Asn Thr Asp Glu Leu Lys
            1090                1095                1100
Phe Ser Asn Cys Val Glu Glu Glu Val Tyr Pro Asn Asn Thr Val Thr
1105                1110                1115                1120
Cys Asn Asp Tyr Thr Ala Thr Gln Glu Glu Tyr Glu Gly Thr Tyr Thr
            1125                1130                1135
Ser Arg Asn Arg Gly Tyr Asp Gly Ala Tyr Glu Ser Asn Ser Ser Val
            1140                1145                1150
Pro Ala Asp Tyr Ala Ser Ala Tyr Glu Glu Lys Ala Tyr Thr Asp Gly
            1155                1160                1165
Arg Arg Asp Asn Pro Cys Glu Ser Asn Arg Gly Tyr Gly Asp Tyr Thr
            1170                1175                1180
Pro Leu Pro Ala Gly Tyr Val Thr Lys Glu Leu Glu Tyr Phe Pro Glu
1185                1190                1195                1200
Thr Asp Lys Val Trp Ile Glu Ile Gly Glu Thr Glu Gly Thr Phe Ile
            1205                1210                1215
Val Asp Ser Val Glu Leu Leu Leu Met Glu Glu
            1220                1225
```

(2) INFORMATION FOR SEQ ID NO:3:

(i) SEQUENCE CHARACTERISTICS:
        (A) LENGTH: 3468 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 1..3468
        (D) OTHER INFORMATION: /product= "Full-length pure maize
           optimized synthetic Bt"

(ix) FEATURE:
(A) NAME/KEY: CDS
(B) LOCATION: 1..3465

(xi) SEQUENCE DESCRIPTION: SEQ ID NO:3:

```
ATG GAC AAC AAC CCC AAC ATC AAC GAG TGC ATC CCC TAC AAC TGC CTG       48
Met Asp Asn Asn Pro Asn Ile Asn Glu Cys Ile Pro Tyr Asn Cys Leu
    1230                1235                1240

AGC AAC CCC GAG GTG GAG GTG CTG GGC GGC GAG CGC ATC GAG ACC GGC       96
Ser Asn Pro Glu Val Glu Val Leu Gly Gly Glu Arg Ile Glu Thr Gly
1245                1250                1255                1260

TAC ACC CCC ATC GAC ATC AGC CTG AGC CTG ACC CAG TTC CTG CTG AGC      144
Tyr Thr Pro Ile Asp Ile Ser Leu Ser Leu Thr Gln Phe Leu Leu Ser
                1265                1270                1275

GAG TTC GTG CCC GGC GCC GGC TTC GTG CTG GGC CTG GTG GAC ATC ATC      192
Glu Phe Val Pro Gly Ala Gly Phe Val Leu Gly Leu Val Asp Ile Ile
            1280                1285                1290

TGG GGC ATC TTC GGC CCC AGC CAG TGG GAC GCC TTC CTG GTG CAG ATC      240
Trp Gly Ile Phe Gly Pro Ser Gln Trp Asp Ala Phe Leu Val Gln Ile
        1295                1300                1305

GAG CAG CTG ATC AAC CAG CGC ATC GAG GAG TTC GCC CGC AAC CAG GCC      288
Glu Gln Leu Ile Asn Gln Arg Ile Glu Glu Phe Ala Arg Asn Gln Ala
    1310                1315                1320

ATC AGC CGC CTG GAG GGC CTG AGC AAC CTG TAC CAG ATC TAC GCC GAG      336
Ile Ser Arg Leu Glu Gly Leu Ser Asn Leu Tyr Gln Ile Tyr Ala Glu
1325                1330                1335                1340

AGC TTC CGC GAG TGG GAG GCC GAC CCC ACC AAC CCC GCC CTG CGC GAG      384
Ser Phe Arg Glu Trp Glu Ala Asp Pro Thr Asn Pro Ala Leu Arg Glu
                1345                1350                1355

GAG ATG CGC ATC CAG TTC AAC GAC ATG AAC AGC GCC CTG ACC ACC GCC      432
Glu Met Arg Ile Gln Phe Asn Asp Met Asn Ser Ala Leu Thr Thr Ala
            1360                1365                1370

ATC CCC CTG TTC GCC GTG CAG AAC TAC CAG GTG CCC CTG CTG AGC GTG      480
Ile Pro Leu Phe Ala Val Gln Asn Tyr Gln Val Pro Leu Leu Ser Val
        1375                1380                1385

TAC GTG CAG GCC GCC AAC CTG CAC CTG AGC GTG CTG CGC GAC GTG AGC      528
Tyr Val Gln Ala Ala Asn Leu His Leu Ser Val Leu Arg Asp Val Ser
    1390                1395                1400

GTG TTC GGC CAG CGC TGG GGC TTC GAC GCC GCC ACC ATC AAC AGC CGC      576
Val Phe Gly Gln Arg Trp Gly Phe Asp Ala Ala Thr Ile Asn Ser Arg
1405                1410                1415                1420

TAC AAC GAC CTG ACC CGC CTG ATC GGC AAC TAC ACC GAC CAC GCC GTG      624
Tyr Asn Asp Leu Thr Arg Leu Ile Gly Asn Tyr Thr Asp His Ala Val
                1425                1430                1435
```

```
CGC TGG TAC AAC ACC GGC CTG GAG CGC GTG TGG GGC CCC GAC AGC CGC        672
Arg Trp Tyr Asn Thr Gly Leu Glu Arg Val Trp Gly Pro Asp Ser Arg
             1440                1445                1450

GAC TGG ATC CGC TAC AAC CAG TTC CGC CGC GAG CTG ACC CTG ACC GTG        720
Asp Trp Ile Arg Tyr Asn Gln Phe Arg Arg Glu Leu Thr Leu Thr Val
             1455                1460                1465

CTG GAC ATC GTG AGC CTG TTC CCC AAC TAC GAC AGC CGC ACC TAC CCC        768
Leu Asp Ile Val Ser Leu Phe Pro Asn Tyr Asp Ser Arg Thr Tyr Pro
             1470                1475                1480

ATC CGC ACC GTG AGC CAG CTG ACC CGC GAG ATC TAC ACC AAC CCC GTG        816
Ile Arg Thr Val Ser Gln Leu Thr Arg Glu Ile Tyr Thr Asn Pro Val
1485             1490                1495                1500

CTG GAG AAC TTC GAC GGC AGC TTC CGC GGC AGC GCC CAG GGC ATC GAG        864
Leu Glu Asn Phe Asp Gly Ser Phe Arg Gly Ser Ala Gln Gly Ile Glu
             1505                1510                1515

GGC AGC ATC CGC AGC CCC CAC CTG ATG GAC ATC CTG AAC AGC ATC ACC        912
Gly Ser Ile Arg Ser Pro His Leu Met Asp Ile Leu Asn Ser Ile Thr
             1520                1525                1530

ATC TAC ACC GAC GCC CAC CGC GGC GAG TAC TAC TGG AGC GGC CAC CAG        960
Ile Tyr Thr Asp Ala His Arg Gly Glu Tyr Tyr Trp Ser Gly His Gln
             1535                1540                1545

ATC ATG GCC AGC CCC GTG GGC TTC AGC GGC CCC GAG TTC ACC TTC CCC       1008
Ile Met Ala Ser Pro Val Gly Phe Ser Gly Pro Glu Phe Thr Phe Pro
             1550                1555                1560

CTG TAC GGC ACC ATG GGC AAC GCC GCC CCC CAG CAG CGC ATC GTG GCC       1056
Leu Tyr Gly Thr Met Gly Asn Ala Ala Pro Gln Gln Arg Ile Val Ala
1565             1570                1575                1580

CAG CTG GGC CAG GGC GTG TAC CGC ACC CTG AGC AGC ACC CTG TAC CGC       1104
Gln Leu Gly Gln Gly Val Tyr Arg Thr Leu Ser Ser Thr Leu Tyr Arg
             1585                1590                1595

CGC CCC TTC AAC ATC GGC ATC AAC AAC CAG CAG CTG AGC GTG CTG GAC       1152
Arg Pro Phe Asn Ile Gly Ile Asn Asn Gln Gln Leu Ser Val Leu Asp
             1600                1605                1610

GGC ACC GAG TTC GCC TAC GGC ACC AGC AGC AAC CTG CCC AGC GCC GTG       1200
Gly Thr Glu Phe Ala Tyr Gly Thr Ser Ser Asn Leu Pro Ser Ala Val
             1615                1620                1625

TAC CGC AAG AGC GGC ACC GTG GAC AGC CTG GAC GAG ATC CCC CCC CAG       1248
Tyr Arg Lys Ser Gly Thr Val Asp Ser Leu Asp Glu Ile Pro Pro Gln
             1630                1635                1640

AAC AAC AAC GTG CCC CCC CGC CAG GGC TTC AGC CAC CGC CTG AGC CAC       1296
Asn Asn Asn Val Pro Pro Arg Gln Gly Phe Ser His Arg Leu Ser His
1645             1650                1655                1660

GTG AGC ATG TTC CGC AGC GGC TTC AGC AAC AGC AGC GTG AGC ATC ATC       1344
Val Ser Met Phe Arg Ser Gly Phe Ser Asn Ser Ser Val Ser Ile Ile
             1665                1670                1675

CGC GCC CCC ATG TTC AGC TGG ATC CAC CGC AGC GCC GAG TTC AAC AAC       1392
Arg Ala Pro Met Phe Ser Trp Ile His Arg Ser Ala Glu Phe Asn Asn
             1680                1685                1690

ATC ATC CCC AGC AGC CAG ATC ACC CAG ATC CCC CTG ACC AAG AGC ACC       1440
Ile Ile Pro Ser Ser Gln Ile Thr Gln Ile Pro Leu Thr Lys Ser Thr
             1695                1700                1705

AAC CTG GGC AGC GGC ACC AGC GTG GTG AAG GGC CCC GGC TTC ACC GGC       1488
Asn Leu Gly Ser Gly Thr Ser Val Val Lys Gly Pro Gly Phe Thr Gly
             1710                1715                1720

GGC GAC ATC CTG CGC CGC ACC AGC CCC GGC CAG ATC AGC ACC CTG CGC       1536
Gly Asp Ile Leu Arg Arg Thr Ser Pro Gly Gln Ile Ser Thr Leu Arg
1725             1730                1735                1740

GTG AAC ATC ACC GCC CCC CTG AGC CAG CGC TAC CGC GTG CGC ATC CGC       1584
Val Asn Ile Thr Ala Pro Leu Ser Gln Arg Tyr Arg Val Arg Ile Arg
             1745                1750                1755
```

-continued

```
TAC GCC AGC ACC ACC AAC CTG CAG TTC CAC ACC AGC ATC GAC GGC CGC      1632
Tyr Ala Ser Thr Thr Asn Leu Gln Phe His Thr Ser Ile Asp Gly Arg
        1760                1765                1770

CCC ATC AAC CAG GGC AAC TTC AGC GCC ACC ATG AGC AGC GGC AGC AAC      1680
Pro Ile Asn Gln Gly Asn Phe Ser Ala Thr Met Ser Ser Gly Ser Asn
            1775                1780                1785

CTG CAG AGC GGC AGC TTC CGC ACC GTG GGC TTC ACC ACC CCC TTC AAC      1728
Leu Gln Ser Gly Ser Phe Arg Thr Val Gly Phe Thr Thr Pro Phe Asn
        1790                1795                1800

TTC AGC AAC GGC AGC AGC GTG TTC ACC CTG AGC GCC CAC GTG TTC AAC      1776
Phe Ser Asn Gly Ser Ser Val Phe Thr Leu Ser Ala His Val Phe Asn
1805                1810                1815                1820

AGC GGC AAC GAG GTG TAC ATC GAC CGC ATC GAG TTC GTG CCC GCC GAG      1824
Ser Gly Asn Glu Val Tyr Ile Asp Arg Ile Glu Phe Val Pro Ala Glu
            1825                1830                1835

GTG ACC TTC GAG GCC GAG TAC GAC CTG GAG CGC GCC CAG AAG GCC GTG      1872
Val Thr Phe Glu Ala Glu Tyr Asp Leu Glu Arg Ala Gln Lys Ala Val
        1840                1845                1850

AAC GAG CTG TTC ACC AGC AGC AAC CAG ATC GGC CTG AAG ACC GAC GTG      1920
Asn Glu Leu Phe Thr Ser Ser Asn Gln Ile Gly Leu Lys Thr Asp Val
    1855                1860                1865

ACC GAC TAC CAC ATC GAC CAG GTG AGC AAC CTG GTG GAG TGC CTG AGC      1968
Thr Asp Tyr His Ile Asp Gln Val Ser Asn Leu Val Glu Cys Leu Ser
        1870                1875                1880

GAC GAG TTC TGC CTG GAC GAG AAG AAG GAG CTG AGC GAG AAG GTG AAG      2016
Asp Glu Phe Cys Leu Asp Glu Lys Lys Glu Leu Ser Glu Lys Val Lys
1885                1890                1895                1900

CAC GCC AAG CGC CTG AGC GAC GAG CGC AAC CTG CTG CAG GAC CCC AAC      2064
His Ala Lys Arg Leu Ser Asp Glu Arg Asn Leu Leu Gln Asp Pro Asn
            1905                1910                1915

TTC CGC GGC ATC AAC CGC CAG CTG GAC CGC GGC TGG CGC GGC AGC ACC      2112
Phe Arg Gly Ile Asn Arg Gln Leu Asp Arg Gly Trp Arg Gly Ser Thr
        1920                1925                1930

GAC ATC ACC ATC CAG GGC GGC GAC GAC GTG TTC AAG GAG AAC TAC GTG      2160
Asp Ile Thr Ile Gln Gly Gly Asp Asp Val Phe Lys Glu Asn Tyr Val
    1935                1940                1945

ACC CTG CTG GGC ACC TTC GAC GAG TGC TAC CCC ACC TAC CTG TAC CAG      2208
Thr Leu Leu Gly Thr Phe Asp Glu Cys Tyr Pro Thr Tyr Leu Tyr Gln
1950                1955                1960

AAG ATC GAC GAG AGC AAG CTG AAG GCC TAC ACC CGC TAC CAG CTG CGC      2256
Lys Ile Asp Glu Ser Lys Leu Lys Ala Tyr Thr Arg Tyr Gln Leu Arg
1965                1970                1975                1980

GGC TAC ATC GAG GAC AGC CAG GAC CTG GAG ATC TAC CTG ATC CGC TAC      2304
Gly Tyr Ile Glu Asp Ser Gln Asp Leu Glu Ile Tyr Leu Ile Arg Tyr
            1985                1990                1995

AAC GCC AAG CAC GAG ACC GTG AAC GTG CCC GGC ACC GGC AGC CTG TGG      2352
Asn Ala Lys His Glu Thr Val Asn Val Pro Gly Thr Gly Ser Leu Trp
        2000                2005                2010

CCC CTG AGC GCC CCC AGC CCC ATC GGC AAG TGC GCC CAC CAC AGC CAC      2400
Pro Leu Ser Ala Pro Ser Pro Ile Gly Lys Cys Ala His His Ser His
            2015                2020                2025

CAC TTC AGC CTG GAC ATC GAC GTG GGC TGC ACC GAC CTG AAC GAG GAC      2448
His Phe Ser Leu Asp Ile Asp Val Gly Cys Thr Asp Leu Asn Glu Asp
        2030                2035                2040

CTG GGC GTG TGG GTG ATC TTC AAG ATC AAG ACC CAG GAC GGC CAC GCC      2496
Leu Gly Val Trp Val Ile Phe Lys Ile Lys Thr Gln Asp Gly His Ala
2045                2050                2055                2060

CGC CTG GGC AAC CTG GAG TTC CTG GAG GAG AAG CCC CTG GTG GGC GAG      2544
Arg Leu Gly Asn Leu Glu Phe Leu Glu Glu Lys Pro Leu Val Gly Glu
```

```
                       2065           2070           2075
GCC CTG GCC CGC GTG AAG CGC GCC GAG AAG AAG TGG CGC GAC AAG CGC    2592
Ala Leu Ala Arg Val Lys Arg Ala Glu Lys Lys Trp Arg Asp Lys Arg
        2080           2085           2090

GAG AAG CTG GAG TGG GAG ACC AAC ATC GTG TAC AAG GAG GCC AAG GAG    2640
Glu Lys Leu Glu Trp Glu Thr Asn Ile Val Tyr Lys Glu Ala Lys Glu
        2095           2100           2105

AGC GTG GAC GCC CTG TTC GTG AAC AGC CAG TAC GAC CGC CTG CAG GCC    2688
Ser Val Asp Ala Leu Phe Val Asn Ser Gln Tyr Asp Arg Leu Gln Ala
        2110           2115           2120

GAC ACC AAC ATC GCC ATG ATC CAC GCC GCC GAC AAG CGC GTG CAC AGC    2736
Asp Thr Asn Ile Ala Met Ile His Ala Ala Asp Lys Arg Val His Ser
2125           2130           2135           2140

ATC CGC GAG GCC TAC CTG CCC GAG CTG AGC GTG ATC CCC GGC GTG AAC    2784
Ile Arg Glu Ala Tyr Leu Pro Glu Leu Ser Val Ile Pro Gly Val Asn
        2145           2150           2155

GCC GCC ATC TTC GAG GAG CTG GAG GGC CGC ATC TTC ACC GCC TTC AGC    2832
Ala Ala Ile Phe Glu Glu Leu Glu Gly Arg Ile Phe Thr Ala Phe Ser
        2160           2165           2170

CTG TAC GAC GCC CGC AAC GTG ATC AAG AAC GGC GAC TTC AAC AAC GGC    2880
Leu Tyr Asp Ala Arg Asn Val Ile Lys Asn Gly Asp Phe Asn Asn Gly
        2175           2180           2185

CTG AGC TGC TGG AAC GTG AAG GGC CAC GTG GAC GTG GAG GAG CAG AAC    2928
Leu Ser Cys Trp Asn Val Lys Gly His Val Asp Val Glu Glu Gln Asn
        2190           2195           2200

AAC CAC CGC AGC GTG CTG GTG GTG CCC GAG TGG GAG GCC GAG GTG AGC    2976
Asn His Arg Ser Val Leu Val Val Pro Glu Trp Glu Ala Glu Val Ser
2205           2210           2215           2220

CAG GAG GTG CGC GTG TGC CCC GGC CGC GGC TAC ATC CTG CGC GTG ACC    3024
Gln Glu Val Arg Val Cys Pro Gly Arg Gly Tyr Ile Leu Arg Val Thr
        2225           2230           2235

GCC TAC AAG GAG GGC TAC GGC GAG GGC TGC GTG ACC ATC CAC GAG ATC    3072
Ala Tyr Lys Glu Gly Tyr Gly Glu Gly Cys Val Thr Ile His Glu Ile
        2240           2245           2250

GAG AAC AAC ACC GAC GAG CTG AAG TTC AGC AAC TGC GTG GAG GAG GAG    3120
Glu Asn Asn Thr Asp Glu Leu Lys Phe Ser Asn Cys Val Glu Glu Glu
        2255           2260           2265

GTG TAC CCC AAC AAC ACC GTG ACC TGC AAC GAC TAC ACC GCC ACC CAG    3168
Val Tyr Pro Asn Asn Thr Val Thr Cys Asn Asp Tyr Thr Ala Thr Gln
        2270           2275           2280

GAG GAG TAC GAG GGC ACC TAC ACC AGC CGC AAC CGC GGC TAC GAC GGC    3216
Glu Glu Tyr Glu Gly Thr Tyr Thr Ser Arg Asn Arg Gly Tyr Asp Gly
2285           2290           2295           2300

GCC TAC GAG AGC AAC AGC AGC GTG CCC GCC GAC TAC GCC AGC GCC TAC    3264
Ala Tyr Glu Ser Asn Ser Ser Val Pro Ala Asp Tyr Ala Ser Ala Tyr
        2305           2310           2315

GAG GAG AAG GCC TAC ACC GAC GGC CGC CGC GAC AAC CCC TGC GAG AGC    3312
Glu Glu Lys Ala Tyr Thr Asp Gly Arg Arg Asp Asn Pro Cys Glu Ser
        2320           2325           2330

AAC CGC GGC TAC GGC GAC TAC ACC CCC CTG CCC GCC GGC TAC GTG ACC    3360
Asn Arg Gly Tyr Gly Asp Tyr Thr Pro Leu Pro Ala Gly Tyr Val Thr
        2335           2340           2345

AAG GAG CTG GAG TAC TTC CCC GAG ACC GAC AAG GTG TGG ATC GAG ATC    3408
Lys Glu Leu Glu Tyr Phe Pro Glu Thr Asp Lys Val Trp Ile Glu Ile
        2350           2355           2360

GGC GAG ACC GAG GGC ACC TTC ATC GTG GAC AGC GTG GAG CTG CTG CTG    3456
Gly Glu Thr Glu Gly Thr Phe Ile Val Asp Ser Val Glu Leu Leu Leu
2365           2370           2375           2380

ATG GAG GAG TAG                                                    3468
```

Met Glu Glu (2) INFORMATION FOR SEQ ID NO:4:

(i) SEQUENCE CHARACTERISTICS:
        (A) LENGTH: 1155 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350
```

-continued

```
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
        370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Val Ser Ile Ile
            435                 440                 445
Arg Ala Pro Met Phe Ser Trp Ile His Arg Ser Ala Glu Phe Asn Asn
        450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
                500                 505                 510
Val Asn Ile Thr Ala Pro Leu Ser Gln Arg Tyr Arg Val Arg Ile Arg
            515                 520                 525
Tyr Ala Ser Thr Thr Asn Leu Gln Phe His Thr Ser Ile Asp Gly Arg
        530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
                580                 585                 590
Ser Gly Asn Glu Val Tyr Ile Asp Arg Ile Glu Phe Val Pro Ala Glu
            595                 600                 605
Val Thr Phe Glu Ala Glu Tyr Asp Leu Glu Arg Ala Gln Lys Ala Val
        610                 615                 620
Asn Glu Leu Phe Thr Ser Ser Asn Gln Ile Gly Leu Lys Thr Asp Val
625                 630                 635                 640
Thr Asp Tyr His Ile Asp Gln Val Ser Asn Leu Val Glu Cys Leu Ser
                645                 650                 655
Asp Glu Phe Cys Leu Asp Glu Lys Lys Glu Leu Ser Glu Lys Val Lys
                660                 665                 670
His Ala Lys Arg Leu Ser Asp Glu Arg Asn Leu Leu Gln Asp Pro Asn
            675                 680                 685
Phe Arg Gly Ile Asn Arg Gln Leu Asp Arg Gly Trp Arg Gly Ser Thr
        690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
                740                 745                 750
Gly Tyr Ile Glu Asp Ser Gln Asp Leu Glu Ile Tyr Leu Ile Arg Tyr
            755                 760                 765
```

-continued

```
Asn Ala Lys His Glu Thr Val Asn Val Pro Gly Thr Gly Ser Leu Trp
    770                 775                 780
Pro Leu Ser Ala Pro Ser Pro Ile Gly Lys Cys Ala His His Ser His
785                 790                 795                 800
His Phe Ser Leu Asp Ile Asp Val Gly Cys Thr Asp Leu Asn Glu Asp
                805                 810                 815
Leu Gly Val Trp Val Ile Phe Lys Ile Lys Thr Gln Asp Gly His Ala
                820                 825                 830
Arg Leu Gly Asn Leu Glu Phe Leu Glu Glu Lys Pro Leu Val Gly Glu
                835                 840                 845
Ala Leu Ala Arg Val Lys Arg Ala Glu Lys Lys Trp Arg Asp Lys Arg
                850                 855                 860
Glu Lys Leu Glu Trp Glu Thr Asn Ile Val Tyr Lys Glu Ala Lys Glu
865                 870                 875                 880
Ser Val Asp Ala Leu Phe Val Asn Ser Gln Tyr Asp Arg Leu Gln Ala
                885                 890                 895
Asp Thr Asn Ile Ala Met Ile His Ala Ala Asp Lys Arg Val His Ser
                900                 905                 910
Ile Arg Glu Ala Tyr Leu Pro Glu Leu Ser Val Ile Pro Gly Val Asn
                915                 920                 925
Ala Ala Ile Phe Glu Glu Leu Glu Gly Arg Ile Phe Thr Ala Phe Ser
                930                 935                 940
Leu Tyr Asp Ala Arg Asn Val Ile Lys Asn Gly Asp Phe Asn Asn Gly
945                 950                 955                 960
Leu Ser Cys Trp Asn Val Lys Gly His Val Asp Val Glu Glu Gln Asn
                965                 970                 975
Asn His Arg Ser Val Leu Val Val Pro Glu Trp Glu Ala Glu Val Ser
                980                 985                 990
Gln Glu Val Arg Val Cys Pro Gly Arg Gly Tyr Ile Leu Arg Val Thr
                995                 1000                1005
Ala Tyr Lys Glu Gly Tyr Gly Glu Gly Cys Val Thr Ile His Glu Ile
                1010                1015                1020
Glu Asn Asn Thr Asp Glu Leu Lys Phe Ser Asn Cys Val Glu Glu Glu
1025                1030                1035                1040
Val Tyr Pro Asn Asn Thr Val Thr Cys Asn Asp Tyr Thr Ala Thr Gln
                1045                1050                1055
Glu Glu Tyr Glu Gly Thr Tyr Thr Ser Arg Asn Arg Gly Tyr Asp Gly
                1060                1065                1070
Ala Tyr Glu Ser Asn Ser Ser Val Pro Ala Asp Tyr Ala Ser Ala Tyr
                1075                1080                1085
Glu Glu Lys Ala Tyr Thr Asp Gly Arg Arg Asp Asn Pro Cys Glu Ser
                1090                1095                1100
Asn Arg Gly Tyr Gly Asp Tyr Thr Pro Leu Pro Ala Gly Tyr Val Thr
1105                1110                1115                1120
Lys Glu Leu Glu Tyr Phe Pro Glu Thr Asp Lys Val Trp Ile Glu Ile
                1125                1130                1135
Gly Glu Thr Glu Gly Thr Phe Ile Val Asp Ser Val Glu Leu Leu Leu
                1140                1145                1150
Met Glu Glu
    1155
```

(2) INFORMATION FOR SEQ ID NO:5:

(i) SEQUENCE CHARACTERISTICS:

-continued

```
        (A) LENGTH: 3468 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 1..3468
        (D) OTHER INFORMATION: /product= "Full length synthetic
            maize optimized"

(ix) FEATURE:
        (A) NAME/KEY: CDS
        (B) LOCATION: 1..3468

(xi) SEQUENCE DESCRIPTION: SEQ ID NO:5:
```

| | | | | | | | | | | | | | | | | |
|---|---|---|---|---|---|---|---|---|---|---|---|---|---|---|---|---|
| ATG | AAC | AAC | CCC | AAC | ATC | AAC | GAG | TGC | ATC | CCC | TAC | AAC | TGC | CTG | | 48 |
| Met | Asp | Asn | Asn | Pro | Asn | Ile | Asn | Glu | Cys | Ile | Pro | Tyr | Asn | Cys | Leu | |
| | | | 1160 | | | | 1165 | | | | 1170 | | | | | |
| AGC | AAC | CCC | GAG | GTG | GAG | GTG | CTG | GGC | GGC | GAG | CGC | ATC | GAG | ACC | GGC | 96 |
| Ser | Asn | Pro | Glu | Val | Glu | Val | Leu | Gly | Gly | Glu | Arg | Ile | Glu | Thr | Gly | |
| | | 1175 | | | | 1180 | | | | 1185 | | | | | | |
| TAC | ACC | CCC | ATC | GAC | ATC | AGC | CTG | AGC | CTG | ACC | CAG | TTC | CTG | CTG | AGC | 144 |
| Tyr | Thr | Pro | Ile | Asp | Ile | Ser | Leu | Ser | Leu | Thr | Gln | Phe | Leu | Leu | Ser | |
| | | 1190 | | | | 1195 | | | | 1200 | | | | | | |
| GAG | TTC | GTG | CCC | GGC | GCC | GGC | TTC | GTG | CTG | GGC | CTG | GTG | GAC | ATC | ATC | 192 |
| Glu | Phe | Val | Pro | Gly | Ala | Gly | Phe | Val | Leu | Gly | Leu | Val | Asp | Ile | Ile | |
| | 1205 | | | | 1210 | | | | 1215 | | | | | | | |
| TGG | GGC | ATC | TTC | GGC | CCC | AGC | CAG | TGG | GAC | GCC | TTC | CTG | GTG | CAG | ATC | 240 |
| Trp | Gly | Ile | Phe | Gly | Pro | Ser | Gln | Trp | Asp | Ala | Phe | Leu | Val | Gln | Ile | |
| 1220 | | | | 1225 | | | | 1230 | | | | 1235 | | | | |
| GAG | CAG | CTG | ATC | AAC | CAG | CGC | ATC | GAG | GAG | TTC | GCC | CGC | AAC | CAG | GCC | 288 |
| Glu | Gln | Leu | Ile | Asn | Gln | Arg | Ile | Glu | Glu | Phe | Ala | Arg | Asn | Gln | Ala | |
| | | | 1240 | | | | 1245 | | | | 1250 | | | | | |
| ATC | AGC | CGC | CTG | GAG | GGC | CTG | AGC | AAC | CTG | TAC | CAA | ATC | TAC | GCC | GAG | 336 |
| Ile | Ser | Arg | Leu | Glu | Gly | Leu | Ser | Asn | Leu | Tyr | Gln | Ile | Tyr | Ala | Glu | |
| | | 1255 | | | | 1260 | | | | 1265 | | | | | | |
| AGC | TTC | CGC | GAG | TGG | GAG | GCC | GAC | CCC | ACC | AAC | CCC | GCC | CTG | CGC | GAG | 384 |
| Ser | Phe | Arg | Glu | Trp | Glu | Ala | Asp | Pro | Thr | Asn | Pro | Ala | Leu | Arg | Glu | |
| | 1270 | | | | 1275 | | | | 1280 | | | | | | | |
| GAG | ATG | CGC | ATC | CAG | TTC | AAC | GAC | ATG | AAC | AGC | GCC | CTG | ACC | ACC | GCC | 432 |
| Glu | Met | Arg | Ile | Gln | Phe | Asn | Asp | Met | Asn | Ser | Ala | Leu | Thr | Thr | Ala | |
| | 1285 | | | | 1290 | | | | 1295 | | | | | | | |
| ATC | CCC | CTG | TTC | GCC | GTG | CAG | AAC | TAC | CAG | GTG | CCC | CTG | CTG | AGC | GTG | 480 |
| Ile | Pro | Leu | Phe | Ala | Val | Gln | Asn | Tyr | Gln | Val | Pro | Leu | Leu | Ser | Val | |
| 1300 | | | | 1305 | | | | 1310 | | | | 1315 | | | | |
| TAC | GTG | CAG | GCC | GCC | AAC | CTG | CAC | CTG | AGC | GTG | CTG | CGC | GAC | GTC | AGC | 528 |
| Tyr | Val | Gln | Ala | Ala | Asn | Leu | His | Leu | Ser | Val | Leu | Arg | Asp | Val | Ser | |
| | | | 1320 | | | | 1325 | | | | 1330 | | | | | |
| GTG | TTC | GGC | CAG | CGC | TGG | GGC | TTC | GAC | GCC | GCC | ACC | ATC | AAC | AGC | CGC | 576 |
| Val | Phe | Gly | Gln | Arg | Trp | Gly | Phe | Asp | Ala | Ala | Thr | Ile | Asn | Ser | Arg | |
| | | 1335 | | | | 1340 | | | | 1345 | | | | | | |
| TAC | AAC | GAC | CTG | ACC | CGC | CTG | ATC | GGC | AAC | TAC | ACC | GAC | CAC | GCC | GTG | 624 |
| Tyr | Asn | Asp | Leu | Thr | Arg | Leu | Ile | Gly | Asn | Tyr | Thr | Asp | His | Ala | Val | |
| | | 1350 | | | | 1355 | | | | 1360 | | | | | | |
| CGC | TGG | TAC | AAC | ACC | GGC | CTG | GAG | CGC | GTG | TGG | GGT | CCC | GAC | AGC | CGC | 672 |
| Arg | Trp | Tyr | Asn | Thr | Gly | Leu | Glu | Arg | Val | Trp | Gly | Pro | Asp | Ser | Arg | |
| | 1365 | | | | 1370 | | | | 1375 | | | | | | | |
| GAC | TGG | ATC | AGG | TAC | AAC | CAG | TTC | CGC | CGC | GAG | CTG | ACC | CTG | ACC | GTG | 720 |

-continued

```
Asp Trp Ile Arg Tyr Asn Gln Phe Arg Arg Glu Leu Thr Leu Thr Val
1380                1385                1390                1395

CTG GAC ATC GTG AGC CTG TTC CCC AAC TAC GAC AGC CGC ACC TAC CCC          768
Leu Asp Ile Val Ser Leu Phe Pro Asn Tyr Asp Ser Arg Thr Tyr Pro
            1400                1405                1410

ATC CGC ACC GTG AGC CAG CTG ACC CGC GAG ATT TAC ACC AAC CCC GTG          816
Ile Arg Thr Val Ser Gln Leu Thr Arg Glu Ile Tyr Thr Asn Pro Val
                1415                1420                1425

CTG GAG AAC TTC GAC GGC AGC TTC CGC GGC AGC GCC CAG GGC ATC GAG          864
Leu Glu Asn Phe Asp Gly Ser Phe Arg Gly Ser Ala Gln Gly Ile Glu
                    1430                1435                1440

GGC AGC ATC CGC AGC CCC CAC CTG ATG GAC ATC CTG AAC AGC ATC ACC          912
Gly Ser Ile Arg Ser Pro His Leu Met Asp Ile Leu Asn Ser Ile Thr
        1445                1450                1455

ATC TAC ACC GAC GCC CAC CGC GGC GAG TAC TAC TGG AGC GGC CAC CAG          960
Ile Tyr Thr Asp Ala His Arg Gly Glu Tyr Tyr Trp Ser Gly His Gln
1460                1465                1470                1475

ATC ATG GCC AGC CCC GTC GGC TTC AGC GGC CCC GAG TTC ACC TTC CCC         1008
Ile Met Ala Ser Pro Val Gly Phe Ser Gly Pro Glu Phe Thr Phe Pro
            1480                1485                1490

CTG TAC GGC ACC ATG GGC AAC GCT GCA CCT CAG CAG CGC ATC GTG GCA         1056
Leu Tyr Gly Thr Met Gly Asn Ala Ala Pro Gln Gln Arg Ile Val Ala
                1495                1500                1505

CAG CTG GGC CAG GGA GTG TAC CGC ACC CTG AGC AGC ACC CTG TAC CGT         1104
Gln Leu Gly Gln Gly Val Tyr Arg Thr Leu Ser Ser Thr Leu Tyr Arg
                    1510                1515                1520

CGA CCT TTC AAC ATC GGC ATC AAC AAC CAG CAG CTG AGC GTG CTG GAC         1152
Arg Pro Phe Asn Ile Gly Ile Asn Asn Gln Gln Leu Ser Val Leu Asp
        1525                1530                1535

GGC ACC GAG TTC GCC TAC GGC ACC AGC AGC AAC CTG CCC AGC GCC GTG         1200
Gly Thr Glu Phe Ala Tyr Gly Thr Ser Ser Asn Leu Pro Ser Ala Val
1540                1545                1550                1555

TAC CGC AAG AGC GGC ACC GTG GAC AGC CTG GAC GAG ATC CCC CCT CAG         1248
Tyr Arg Lys Ser Gly Thr Val Asp Ser Leu Asp Glu Ile Pro Pro Gln
            1560                1565                1570

AAC AAC AAC GTG CCA CCT CGA CAG GGC TTC AGC CAC CGT CTG AGC CAC         1296
Asn Asn Asn Val Pro Pro Arg Gln Gly Phe Ser His Arg Leu Ser His
                1575                1580                1585

GTG AGC ATG TTC CGC AGT GGC TTC AGC AAC AGC AGC GTG AGC ATC ATC         1344
Val Ser Met Phe Arg Ser Gly Phe Ser Asn Ser Ser Val Ser Ile Ile
                    1590                1595                1600

CGT GCA CCT ATG TTC AGC TGG ATT CAC CGC AGT GCC GAG TTC AAC AAC         1392
Arg Ala Pro Met Phe Ser Trp Ile His Arg Ser Ala Glu Phe Asn Asn
        1605                1610                1615

ATC ATC CCC AGC AGC CAG ATC ACC CAG ATC CCC CTG ACC AAG AGC ACC         1440
Ile Ile Pro Ser Ser Gln Ile Thr Gln Ile Pro Leu Thr Lys Ser Thr
1620                1625                1630                1635

AAC CTG GGC AGC GGC ACC AGC GTG GTG AAG GGC CCC GGC TTC ACC GGC         1488
Asn Leu Gly Ser Gly Thr Ser Val Val Lys Gly Pro Gly Phe Thr Gly
            1640                1645                1650

GGC GAC ATC CTG CGC CGC ACC AGC CCC GGC CAG ATC AGC ACC CTG CGC         1536
Gly Asp Ile Leu Arg Arg Thr Ser Pro Gly Gln Ile Ser Thr Leu Arg
                1655                1660                1665

GTG AAC ATC ACC GCC CCC CTG AGC CAG CGC TAC CGC GTC CGC ATC CGC         1584
Val Asn Ile Thr Ala Pro Leu Ser Gln Arg Tyr Arg Val Arg Ile Arg
                    1670                1675                1680

TAC GCC AGC ACC ACC AAC CTG CAG TTC CAC ACC AGC ATC GAC GGC CGC         1632
Tyr Ala Ser Thr Thr Asn Leu Gln Phe His Thr Ser Ile Asp Gly Arg
        1685                1690                1695
```

-continued

```
CCC ATC AAC CAG GGC AAC TTC AGC GCC ACC ATG AGC AGC GGC AGC AAC        1680
Pro Ile Asn Gln Gly Asn Phe Ser Ala Thr Met Ser Ser Gly Ser Asn
1700                1705                1710                1715

CTG CAG AGC GGC AGC TTC CGC ACC GTG GGC TTC ACC ACC CCC TTC AAC        1728
Leu Gln Ser Gly Ser Phe Arg Thr Val Gly Phe Thr Thr Pro Phe Asn
                1720                1725                1730

TTC AGC AAC GGC AGC AGC GTG TTC ACC CTG AGC GCC CAC GTG TTC AAC        1776
Phe Ser Asn Gly Ser Ser Val Phe Thr Leu Ser Ala His Val Phe Asn
            1735                1740                1745

AGC GGC AAC GAG GTG TAC ATC GAC CGC ATC GAG TTC GTG CCC GCC GAG        1824
Ser Gly Asn Glu Val Tyr Ile Asp Arg Ile Glu Phe Val Pro Ala Glu
            1750                1755                1760

GTG ACC TTC GAG GCC GAG TAC GAC CTG GAG AGG GCT CAG AAG GCC GTG        1872
Val Thr Phe Glu Ala Glu Tyr Asp Leu Glu Arg Ala Gln Lys Ala Val
        1765                1770                1775

AAC GAG CTG TTC ACC AGC AGC AAC CAG ATC GGC CTG AAG ACC GAC GTG        1920
Asn Glu Leu Phe Thr Ser Ser Asn Gln Ile Gly Leu Lys Thr Asp Val
1780                1785                1790                1795

ACC GAC TAC CAC ATC GAT CAG GTG AGC AAC CTG GTG GAG TGC CTG AGC        1968
Thr Asp Tyr His Ile Asp Gln Val Ser Asn Leu Val Glu Cys Leu Ser
                1800                1805                1810

GAC GAG TTC TGC CTG GAC GAG AAG AAG GAG CTG AGC GAG AAG GTG AAG        2016
Asp Glu Phe Cys Leu Asp Glu Lys Lys Glu Leu Ser Glu Lys Val Lys
            1815                1820                1825

CAC GCC AAG CGC CTG AGC GAC GAG CGC AAC CTG CTG CAG GAC CCC AAC        2064
His Ala Lys Arg Leu Ser Asp Glu Arg Asn Leu Leu Gln Asp Pro Asn
            1830                1835                1840

TTC CGC GGC ATC AAC CGC CAG CTG GAC CGC GGC TGG CGC GGC AGC ACC        2112
Phe Arg Gly Ile Asn Arg Gln Leu Asp Arg Gly Trp Arg Gly Ser Thr
        1845                1850                1855

GAC ATC ACC ATC CAG GGC GGC GAC GAC GTG TTC AAG GAG AAC TAC GTG        2160
Asp Ile Thr Ile Gln Gly Gly Asp Asp Val Phe Lys Glu Asn Tyr Val
1860                1865                1870                1875

ACC CTG CTG GGC ACC TTC GAC GAG TGC TAC CCC ACC TAC CTG TAC CAG        2208
Thr Leu Leu Gly Thr Phe Asp Glu Cys Tyr Pro Thr Tyr Leu Tyr Gln
                1880                1885                1890

AAG ATC GAC GAG AGC AAG CTG AAG GCC TAC ACC CGC TAC CAG CTG CGC        2256
Lys Ile Asp Glu Ser Lys Leu Lys Ala Tyr Thr Arg Tyr Gln Leu Arg
            1895                1900                1905

GGC TAC ATC GAG GAC AGC CAG GAC CTG GAG ATC TAC CTG ATC CGC TAC        2304
Gly Tyr Ile Glu Asp Ser Gln Asp Leu Glu Ile Tyr Leu Ile Arg Tyr
        1910                1915                1920

AAC GCC AAG CAC GAG ACC GTG AAC GTG CCC GGC ACC GGC AGC CTG TGG        2352
Asn Ala Lys His Glu Thr Val Asn Val Pro Gly Thr Gly Ser Leu Trp
1925                1930                1935

CCC CTG AGC GCC CCC AGC CCC ATC GGC AAG TGC GCC CAC CAC AGC CAC        2400
Pro Leu Ser Ala Pro Ser Pro Ile Gly Lys Cys Ala His His Ser His
1940                1945                1950                1955

CAC TTC AGC CTG GAC ATC GAC GTG GGC TGC ACC GAC CTG AAC GAG GAC        2448
His Phe Ser Leu Asp Ile Asp Val Gly Cys Thr Asp Leu Asn Glu Asp
                1960                1965                1970

CTG GGC GTG TGG GTG ATC TTC AAG ATC AAG ACC CAG GAC GGC CAC GCC        2496
Leu Gly Val Trp Val Ile Phe Lys Ile Lys Thr Gln Asp Gly His Ala
            1975                1980                1985

CGC CTG GGC AAC CTG GAG TTC CTG GAG GAG AAG CCC CTG GTG GGC GAG        2544
Arg Leu Gly Asn Leu Glu Phe Leu Glu Glu Lys Pro Leu Val Gly Glu
        1990                1995                2000

GCC CTG GCC CGC GTG AAG CGC GCC GAG AAG AAG TGG CGC GAC AAG CGC        2592
Ala Leu Ala Arg Val Lys Arg Ala Glu Lys Lys Trp Arg Asp Lys Arg
    2005                2010                2015
```

-continued

```
GAG AAG CTG GAG TGG GAG ACC AAC ATC GTG TAC AAG GAG GCC AAG GAG     2640
Glu Lys Leu Glu Trp Glu Thr Asn Ile Val Tyr Lys Glu Ala Lys Glu
2020                2025                2030                2035

AGC GTG GAC GCC CTG TTC GTG AAC AGC CAG TAC GAC CGC CTG CAG GCC     2688
Ser Val Asp Ala Leu Phe Val Asn Ser Gln Tyr Asp Arg Leu Gln Ala
            2040                2045                2050

GAC ACC AAC ATC GCC ATG ATC CAC GCC GCC GAC AAG CGC GTG CAC AGC     2736
Asp Thr Asn Ile Ala Met Ile His Ala Ala Asp Lys Arg Val His Ser
        2055                2060                2065

ATT CGC GAG GCC TAC CTG CCC GAG CTG AGC GTG ATC CCC GGC GTG AAC     2784
Ile Arg Glu Ala Tyr Leu Pro Glu Leu Ser Val Ile Pro Gly Val Asn
    2070                2075                2080

GCC GCC ATC TTC GAG GAG CTG GAG GGC CGC ATC TTC ACC GCC TTC AGC     2832
Ala Ala Ile Phe Glu Glu Leu Glu Gly Arg Ile Phe Thr Ala Phe Ser
2085                2090                2095

CTG TAC GAC GCC CGC AAC GTG ATC AAG AAC GGC GAC TTC AAC AAC GGC     2880
Leu Tyr Asp Ala Arg Asn Val Ile Lys Asn Gly Asp Phe Asn Asn Gly
2100                2105                2110                2115

CTG AGC TGC TGG AAC GTG AAG GGC CAC GTG GAC GTG GAG GAG CAG AAC     2928
Leu Ser Cys Trp Asn Val Lys Gly His Val Asp Val Glu Glu Gln Asn
            2120                2125                2130

AAC CAC CGC AGC GTG CTG GTG GTG CCC GAG TGG GAG GCC GAG GTG AGC     2976
Asn His Arg Ser Val Leu Val Val Pro Glu Trp Glu Ala Glu Val Ser
        2135                2140                2145

CAG GAG GTG CGC GTG TGC CCC GGC CGC GGC TAC ATC CTG CGC GTG ACC     3024
Gln Glu Val Arg Val Cys Pro Gly Arg Gly Tyr Ile Leu Arg Val Thr
    2150                2155                2160

GCC TAC AAG GAG GGC TAC GGC GAG GGC TGC GTG ACC ATC CAC GAG ATC     3072
Ala Tyr Lys Glu Gly Tyr Gly Glu Gly Cys Val Thr Ile His Glu Ile
2165                2170                2175

GAG AAC AAC ACC GAC GAG CTC AAG TTC AGC AAC TGC GTG GAG GAG GAG     3120
Glu Asn Asn Thr Asp Glu Leu Lys Phe Ser Asn Cys Val Glu Glu Glu
2180                2185                2190                2195

GTG TAC CCC AAC AAC ACC GTG ACC TGC AAC GAC TAC ACC GCC ACC CAG     3168
Val Tyr Pro Asn Asn Thr Val Thr Cys Asn Asp Tyr Thr Ala Thr Gln
            2200                2205                2210

GAG GAG TAC GAG GGC ACC TAC ACC AGC CGC AAC CGC GGC TAC GAC GGC     3216
Glu Glu Tyr Glu Gly Thr Tyr Thr Ser Arg Asn Arg Gly Tyr Asp Gly
        2215                2220                2225

GCC TAC GAG AGC AAC AGC AGC GTG CCC GCC GAC TAC GCC AGC GCC TAC     3264
Ala Tyr Glu Ser Asn Ser Ser Val Pro Ala Asp Tyr Ala Ser Ala Tyr
    2230                2235                2240

GAG GAG AAG GCC TAC ACC GAC GGC CGC CGC GAC AAC CCC TGC GAG AGC     3312
Glu Glu Lys Ala Tyr Thr Asp Gly Arg Arg Asp Asn Pro Cys Glu Ser
2245                2250                2255

AAC CGC GGC TAC GGC GAC TAC ACC CCC CTG CCC GCC GGC TAC GTG ACC     3360
Asn Arg Gly Tyr Gly Asp Tyr Thr Pro Leu Pro Ala Gly Tyr Val Thr
2260                2265                2270                2275

AAG GAG CTG GAG TAC TTC CCC GAG ACC GAC AAG GTG TGG ATC GAG ATC     3408
Lys Glu Leu Glu Tyr Phe Pro Glu Thr Asp Lys Val Trp Ile Glu Ile
            2280                2285                2290

GGC GAG ACC GAG GGC ACC TTC ATC GTG GAC AGC GTG GAG CTG CTG CTG     3456
Gly Glu Thr Glu Gly Thr Phe Ile Val Asp Ser Val Glu Leu Leu Leu
        2295                2300                2305

ATG GAG GAG TAG                                                     3468
Met Glu Glu *
    2310
```

(2) INFORMATION FOR SEQ ID NO:6:

(i) SEQUENCE CHARACTERISTICS:
    (A) LENGTH: 1155 amino acids
    (B) TYPE: amino acid
    (D) TOPOLOGY: linear (ii) MOLECULE TYPE: protein (xi) SEQUENCE DESCRIPTION: SEQ ID NO:6:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365
```

```
Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
        530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Ala His His Ser His
```

```
                     785                 790                 795                 800
His Phe Ser Leu Asp Ile Asp Val Gly Cys Thr Asp Leu Asn Glu Asp
                 805                 810                 815

Leu Gly Val Trp Val Ile Phe Lys Ile Lys Thr Gln Asp Gly His Ala
                 820                 825                 830

Arg Leu Gly Asn Leu Glu Phe Leu Glu Glu Lys Pro Leu Val Gly Glu
                 835                 840                 845

Ala Leu Ala Arg Val Lys Arg Ala Glu Lys Lys Trp Arg Asp Lys Arg
                 850                 855                 860

Glu Lys Leu Glu Trp Glu Thr Asn Ile Val Tyr Lys Glu Ala Lys Glu
865                  870                 875                 880

Ser Val Asp Ala Leu Phe Val Asn Ser Gln Tyr Asp Arg Leu Gln Ala
                 885                 890                 895

Asp Thr Asn Ile Ala Met Ile His Ala Ala Asp Lys Arg Val His Ser
                 900                 905                 910

Ile Arg Glu Ala Tyr Leu Pro Glu Leu Ser Val Ile Pro Gly Val Asn
                 915                 920                 925

Ala Ala Ile Phe Glu Glu Leu Glu Gly Arg Ile Phe Thr Ala Phe Ser
                 930                 935                 940

Leu Tyr Asp Ala Arg Asn Val Ile Lys Asn Gly Asp Phe Asn Asn Gly
945                  950                 955                 960

Leu Ser Cys Trp Asn Val Lys Gly His Val Asp Val Glu Glu Gln Asn
                 965                 970                 975

Asn His Arg Ser Val Leu Val Pro Glu Trp Glu Ala Glu Val Ser
                 980                 985                 990

Gln Glu Val Arg Val Cys Pro Gly Arg Gly Tyr Ile Leu Arg Val Thr
                 995                 1000                1005

Ala Tyr Lys Glu Gly Tyr Gly Glu Gly Cys Val Thr Ile His Glu Ile
                 1010                1015                1020

Glu Asn Asn Thr Asp Glu Leu Lys Phe Ser Asn Cys Val Glu Glu Glu
1025                 1030                1035                1040

Val Tyr Pro Asn Asn Thr Val Thr Cys Asn Asp Tyr Thr Ala Thr Gln
                 1045                1050                1055

Glu Glu Tyr Glu Gly Thr Tyr Thr Ser Arg Asn Arg Gly Tyr Asp Gly
                 1060                1065                1070

Ala Tyr Glu Ser Asn Ser Ser Val Pro Ala Asp Tyr Ala Ser Ala Tyr
                 1075                1080                1085

Glu Glu Lys Ala Tyr Thr Asp Gly Arg Arg Asp Asn Pro Cys Glu Ser
                 1090                1095                1100

Asn Arg Gly Tyr Gly Asp Tyr Thr Pro Leu Pro Ala Gly Tyr Val Thr
1105                 1110                1115                1120

Lys Glu Leu Glu Tyr Phe Pro Glu Thr Asp Lys Val Trp Ile Glu Ile
                 1125                1130                1135

Gly Glu Thr Glu Gly Thr Phe Ile Val Asp Ser Val Glu Leu Leu Leu
                 1140                1145                1150

Met Glu Glu
        1155

(2) INFORMATION FOR SEQ ID NO:7:

(i) SEQUENCE CHARACTERISTICS:
        (A) LENGTH: 3624 base pairs
        (B) TYPE: nucleic acid
        (C) STRANDEDNESS: single
        (D) TOPOLOGY: linear
```

-continued (ii) MOLECULE TYPE: other nucleic acid
(A) DESCRIPTION: /desc = "Synthetic DNA"

(iii) HYPOTHETICAL: NO (ix) FEATURE:
(A) NAME/KEY: CDS
(B) LOCATION: 1..3621
(D) OTHER INFORMATION: /product= "Full-length, maize optmized cryIB"
/note= "Disclosed in Figure 6."

(xi) SEQUENCE DESCRIPTION: SEQ ID NO:7:

```
ATG GAC CTG CTG CCC GAC GCC CGC ATC GAG GAC AGC CTG TGC ATC GCC       48
Met Asp Leu Leu Pro Asp Ala Arg Ile Glu Asp Ser Leu Cys Ile Ala
            1160                1165                1170

GAG GGC AAC AAC ATC GAC CCC TTC GTG AGC GCC AGC ACC GTG CAG ACC       96
Glu Gly Asn Asn Ile Asp Pro Phe Val Ser Ala Ser Thr Val Gln Thr
        1175                1180                1185

GGC ATC AAC ATC GCC GGC CGC ATC CTG GGC GTG CTG GGC GTG CCC TTC      144
Gly Ile Asn Ile Ala Gly Arg Ile Leu Gly Val Leu Gly Val Pro Phe
    1190                1195                1200

GCC GGC CAG CTG GCC AGC TTC TAC AGC TTC CTG GTG GGC GAG CTG TGG      192
Ala Gly Gln Leu Ala Ser Phe Tyr Ser Phe Leu Val Gly Glu Leu Trp
1205                1210                1215                1220

CCC CGC GGC CGC GAC CAG TGG GAG ATC TTC CTG GAG CAC GTG GAG CAG      240
Pro Arg Gly Arg Asp Gln Trp Glu Ile Phe Leu Glu His Val Glu Gln
                1225                1230                1235

CTG ATC AAC CAG CAG ATC ACC GAG AAC GCC CGC AAC ACC GCC CTG GCC      288
Leu Ile Asn Gln Gln Ile Thr Glu Asn Ala Arg Asn Thr Ala Leu Ala
            1240                1245                1250

CGC CTG CAG GGC CTG GGC GAC AGC TTC CGC GCC TAC CAG CAG AGC CTG      336
Arg Leu Gln Gly Leu Gly Asp Ser Phe Arg Ala Tyr Gln Gln Ser Leu
        1255                1260                1265

GAG GAC TGG CTG GAG AAC CGC GAC GAC GCC CGC ACC CGC AGC GTG CTG      384
Glu Asp Trp Leu Glu Asn Arg Asp Asp Ala Arg Thr Arg Ser Val Leu
    1270                1275                1280

TAC ACC CAG TAC ATC GCC CTG GAG CTG GAC TTC CTG AAC GCC ATG CCC      432
Tyr Thr Gln Tyr Ile Ala Leu Glu Leu Asp Phe Leu Asn Ala Met Pro
1285                1290                1295                1300

CTG TTC GCC ATC CGC AAC CAG GAG GTG CCC CTG CTG ATG GTG TAC GCC      480
Leu Phe Ala Ile Arg Asn Gln Glu Val Pro Leu Leu Met Val Tyr Ala
                1305                1310                1315

CAG GCC GCC AAC CTG CAC CTG CTG CTG CTG CGC GAC GCC AGC CTG TTC      528
Gln Ala Ala Asn Leu His Leu Leu Leu Leu Arg Asp Ala Ser Leu Phe
            1320                1325                1330

GGC AGC GAG TTC GGC CTG ACC AGC CAG GAG ATC CAG CGC TAC TAC GAG      576
Gly Ser Glu Phe Gly Leu Thr Ser Gln Glu Ile Gln Arg Tyr Tyr Glu
        1335                1340                1345

CGC CAG GTG GAG CGC ACC CGC GAC TAC AGC GAC TAC TGC GTG GAG TGG      624
Arg Gln Val Glu Arg Thr Arg Asp Tyr Ser Asp Tyr Cys Val Glu Trp
    1350                1355                1360

TAC AAC ACC GGC CTG AAC AGC CTG CGC GGC ACC AAC GCC GCC AGC TGG      672
Tyr Asn Thr Gly Leu Asn Ser Leu Arg Gly Thr Asn Ala Ala Ser Trp
1365                1370                1375                1380

GTG CGC TAC AAC CAG TTC CGC CGC GAC CTG ACC CTG GGC GTG CTG GAC      720
Val Arg Tyr Asn Gln Phe Arg Arg Asp Leu Thr Leu Gly Val Leu Asp
                1385                1390                1395

CTG GTG GCC CTG TTC CCC AGC TAC GAC ACC CGC ACC TAC CCC ATC AAC      768
Leu Val Ala Leu Phe Pro Ser Tyr Asp Thr Arg Thr Tyr Pro Ile Asn
            1400                1405                1410
```

-continued

```
ACC AGC GCC CAG CTG ACC CGC GAG GTG TAC ACC GAC GCC ATC GGC GCC        816
Thr Ser Ala Gln Leu Thr Arg Glu Val Tyr Thr Asp Ala Ile Gly Ala
        1415                1420                1425

ACC GGC GTG AAC ATG GCC AGC ATG AAC TGG TAC AAC AAC AAC GCC CCC        864
Thr Gly Val Asn Met Ala Ser Met Asn Trp Tyr Asn Asn Asn Ala Pro
        1430                1435                1440

AGC TTC AGC GCC ATC GAG GCC GCC GCC ATC CGC AGC CCC CAC CTG CTG        912
Ser Phe Ser Ala Ile Glu Ala Ala Ala Ile Arg Ser Pro His Leu Leu
1445                1450                1455                1460

GAC TTC CTG GAG CAG CTG ACC ATC TTC AGC GCC AGC AGC CGC TGG AGC        960
Asp Phe Leu Glu Gln Leu Thr Ile Phe Ser Ala Ser Ser Arg Trp Ser
                1465                1470                1475

AAC ACC CGC CAC ATG ACC TAC TGG CGC GGC CAC ACC ATC CAG AGC CGC       1008
Asn Thr Arg His Met Thr Tyr Trp Arg Gly His Thr Ile Gln Ser Arg
        1480                1485                1490

CCC ATC GGC GGC GGC CTG AAC ACC AGC ACC CAC GGC GCC ACC AAC ACC       1056
Pro Ile Gly Gly Gly Leu Asn Thr Ser Thr His Gly Ala Thr Asn Thr
        1495                1500                1505

AGC ATC AAC CCC GTG ACC CTG CGC TTC GCC AGC CGC GAC GTG TAC CGC       1104
Ser Ile Asn Pro Val Thr Leu Arg Phe Ala Ser Arg Asp Val Tyr Arg
        1510                1515                1520

ACC GAG AGC TAC GCC GGC GTG CTG CTG TGG GGC ATC TAC CTG GAG CCC       1152
Thr Glu Ser Tyr Ala Gly Val Leu Leu Trp Gly Ile Tyr Leu Glu Pro
1525                1530                1535                1540

ATC CAC GGC GTG CCC ACC GTG CGC TTC AAC TTC ACC AAC CCC CAG AAC       1200
Ile His Gly Val Pro Thr Val Arg Phe Asn Phe Thr Asn Pro Gln Asn
                1545                1550                1555

ATC AGC GAC CGC GGC ACC GCC AAC TAC AGC CAG CCC TAC GAG AGC CCC       1248
Ile Ser Asp Arg Gly Thr Ala Asn Tyr Ser Gln Pro Tyr Glu Ser Pro
        1560                1565                1570

GGC CTG CAG CTG AAG GAC AGC GAG ACC GAG CTG CCC CCC GAG ACC ACC       1296
Gly Leu Gln Leu Lys Asp Ser Glu Thr Glu Leu Pro Pro Glu Thr Thr
        1575                1580                1585

GAG CGC CCC AAC TAC GAG AGC TAC AGC CAC CGC CTG AGC CAC ATC GGC       1344
Glu Arg Pro Asn Tyr Glu Ser Tyr Ser His Arg Leu Ser His Ile Gly
        1590                1595                1600

ATC ATC CTG CAG AGC CGC GTG AAC GTG CCC GTG TAC AGC TGG ACC CAC       1392
Ile Ile Leu Gln Ser Arg Val Asn Val Pro Val Tyr Ser Trp Thr His
1605                1610                1615                1620

CGC AGC GCC GAC CGC ACC AAC ACC ATC GGC CCC AAC CGC ATC ACC CAG       1440
Arg Ser Ala Asp Arg Thr Asn Thr Ile Gly Pro Asn Arg Ile Thr Gln
                1625                1630                1635

ATC CCC ATG GTG AAG GCC AGC GAG CTG CCC CAG GGC ACC ACC GTG GTG       1488
Ile Pro Met Val Lys Ala Ser Glu Leu Pro Gln Gly Thr Thr Val Val
        1640                1645                1650

CGC GGC CCC GGC TTC ACC GGC GGC GAC ATC CTG CGC CGC ACC AAC ACC       1536
Arg Gly Pro Gly Phe Thr Gly Gly Asp Ile Leu Arg Arg Thr Asn Thr
        1655                1660                1665

GGC GGC TTC GGC CCC ATC CGC GTG ACC GTG AAC GGC CCC CTG ACC CAG       1584
Gly Gly Phe Gly Pro Ile Arg Val Thr Val Asn Gly Pro Leu Thr Gln
        1670                1675                1680

CGC TAC CGC ATC GGC TTC CGC TAC GCC AGC ACC GTG GAC TTC GAC TTC       1632
Arg Tyr Arg Ile Gly Phe Arg Tyr Ala Ser Thr Val Asp Phe Asp Phe
1685                1690                1695                1700

TTC GTG AGC CGC GGC GGC ACC ACC GTG AAC AAC TTC CGC TTC CTG CGC       1680
Phe Val Ser Arg Gly Gly Thr Thr Val Asn Asn Phe Arg Phe Leu Arg
                1705                1710                1715

ACC ATG AAC AGC GGC GAC GAG CTG AAG TAC GGC AAC TTC GTG CGC CGC       1728
Thr Met Asn Ser Gly Asp Glu Leu Lys Tyr Gly Asn Phe Val Arg Arg
        1720                1725                1730
```

```
GCC TTC ACC ACC CCC TTC ACC TTC ACC CAG ATC CAG GAC ATC ATC CGC    1776
Ala Phe Thr Thr Pro Phe Thr Phe Thr Gln Ile Gln Asp Ile Ile Arg
            1735                1740                1745

ACC AGC ATC CAG GGC CTG AGC GGC AAC GGC GAG GTG TAC ATC GAC AAG    1824
Thr Ser Ile Gln Gly Leu Ser Gly Asn Gly Glu Val Tyr Ile Asp Lys
        1750                1755                1760

ATC GAG ATC ATC CCC GTG ACC GCC ACC TTC GAG GCC GAG TAC GAC CTG    1872
Ile Glu Ile Ile Pro Val Thr Ala Thr Phe Glu Ala Glu Tyr Asp Leu
1765                1770                1775                1780

GAG CGC GCC CAG GAG GCC GTG AAC GCC CTG TTC ACC AAC ACC AAC CCC    1920
Glu Arg Ala Gln Glu Ala Val Asn Ala Leu Phe Thr Asn Thr Asn Pro
                1785                1790                1795

CGC CGC CTG AAG ACC GAC GTG ACC GAC TAC CAC ATC GAC CAG GTG AGC    1968
Arg Arg Leu Lys Thr Asp Val Thr Asp Tyr His Ile Asp Gln Val Ser
            1800                1805                1810

AAC CTG GTG GCC TGC CTG AGC GAC GAG TTC TGC CTG GAC GAG AAG CGC    2016
Asn Leu Val Ala Cys Leu Ser Asp Glu Phe Cys Leu Asp Glu Lys Arg
        1815                1820                1825

GAG CTG CTG GAG AAG GTG AAG TAC GCC AAG CGC CTG AGC GAC GAG CGC    2064
Glu Leu Leu Glu Lys Val Lys Tyr Ala Lys Arg Leu Ser Asp Glu Arg
    1830                1835                1840

AAC CTG CTG CAG GAC CCC AAC TTC ACC AGC ATC AAC AAG CAG CCC GAC    2112
Asn Leu Leu Gln Asp Pro Asn Phe Thr Ser Ile Asn Lys Gln Pro Asp
1845                1850                1855                1860

TTC ATC AGC ACC AAC GAG CAG AGC AAC TTC ACC AGC ATC CAC GAG CAG    2160
Phe Ile Ser Thr Asn Glu Gln Ser Asn Phe Thr Ser Ile His Glu Gln
                1865                1870                1875

AGC GAG CAC GGC TGG TGG GGC AGC GAG AAC ATC ACC ATC CAG GAG GGC    2208
Ser Glu His Gly Trp Trp Gly Ser Glu Asn Ile Thr Ile Gln Glu Gly
            1880                1885                1890

AAC GAC GTG TTC AAG GAG AAC TAC GTG ACC CTG CCC GGC ACC TTC AAC    2256
Asn Asp Val Phe Lys Glu Asn Tyr Val Thr Leu Pro Gly Thr Phe Asn
        1895                1900                1905

GAG TGC TAC CCC ACC TAC CTG TAC CAG AAG ATC GGC GAG AGC GAG CTG    2304
Glu Cys Tyr Pro Thr Tyr Leu Tyr Gln Lys Ile Gly Glu Ser Glu Leu
    1910                1915                1920

AAG GCC TAC ACC CGC TAC CAG CTG CGC GGC TAC ATC GAG GAC AGC CAG    2352
Lys Ala Tyr Thr Arg Tyr Gln Leu Arg Gly Tyr Ile Glu Asp Ser Gln
1925                1930                1935                1940

GAC CTG GAG ATC TAC CTG ATC CGC TAC AAC GCC AAG CAC GAG ACC CTG    2400
Asp Leu Glu Ile Tyr Leu Ile Arg Tyr Asn Ala Lys His Glu Thr Leu
                1945                1950                1955

GAC GTG CCC GGC ACC GAG AGC CTG TGG CCC CTG AGC GTG GAG AGC CCC    2448
Asp Val Pro Gly Thr Glu Ser Leu Trp Pro Leu Ser Val Glu Ser Pro
            1960                1965                1970

ATC GGC CGC TGC GGC GAG CCC AAC CGC TGC GCC CCC CAC TTC GAG TGG    2496
Ile Gly Arg Cys Gly Glu Pro Asn Arg Cys Ala Pro His Phe Glu Trp
        1975                1980                1985

AAC CCC GAC CTG GAC TGC AGC TGC CGC GAC GGC GAG AAG TGC GCC CAC    2544
Asn Pro Asp Leu Asp Cys Ser Cys Arg Asp Gly Glu Lys Cys Ala His
    1990                1995                2000

CAC AGC CAC CAC TTC AGC CTG GAC ATC GAC GTG GGC TGC ACC GAC CTG    2592
His Ser His His Phe Ser Leu Asp Ile Asp Val Gly Cys Thr Asp Leu
2005                2010                2015                2020

CAC GAG AAC CTG GGC GTG TGG GTG GTG TTC AAG ATC AAG ACC CAG GAG    2640
His Glu Asn Leu Gly Val Trp Val Val Phe Lys Ile Lys Thr Gln Glu
                2025                2030                2035

GGC CAC GCC CGC CTG GGC AAC CTG GAG TTC ATC GAG GAG AAG CCC CTG    2688
Gly His Ala Arg Leu Gly Asn Leu Glu Phe Ile Glu Glu Lys Pro Leu
```

|  |  |
|---|---|
| CTG GGC GAG GCC CTG AGC CGC GTG AAG CGC GCC GAG AAG AAG TGG CGC<br>Leu Gly Glu Ala Leu Ser Arg Val Lys Arg Ala Glu Lys Lys Trp Arg<br>      2055                     2060                  2065 | 2736 |
| GAC AAG CGC GAG AAG CTG CAG CTG GAG ACC AAG CGC GTG TAC ACC GAG<br>Asp Lys Arg Glu Lys Leu Gln Leu Glu Thr Lys Arg Val Tyr Thr Glu<br>2070                 2075                  2080 | 2784 |
| GCC AAG GAG GCC GTG GAC GCC CTG TTC GTG GAC AGC CAG TAC GAC CGC<br>Ala Lys Glu Ala Val Asp Ala Leu Phe Val Asp Ser Gln Tyr Asp Arg<br>2085               2090                 2095               2100 | 2832 |
| CTG CAG GCC GAC ACC AAC ATC GGC ATG ATC CAC GCC GCC GAC AAG CTG<br>Leu Gln Ala Asp Thr Asn Ile Gly Met Ile His Ala Ala Asp Lys Leu<br>              2105                  2110                2115 | 2880 |
| GTG CAC CGC ATC CGC GAG GCC TAC CTG AGC GAG CTG CCC GTG ATC CCC<br>Val His Arg Ile Arg Glu Ala Tyr Leu Ser Glu Leu Pro Val Ile Pro<br>      2120                   2125                  2130 | 2928 |
| GGC GTG AAC GCC GAG ATC TTC GAG GAG CTG GAG GGC CAC ATC ATC ACC<br>Gly Val Asn Ala Glu Ile Phe Glu Glu Leu Glu Gly His Ile Ile Thr<br>              2135                  2140                2145 | 2976 |
| GCC ATC AGC CTG TAC GAC GCC CGC AAC GTG GTG AAG AAC GGC GAC TTC<br>Ala Ile Ser Leu Tyr Asp Ala Arg Asn Val Val Lys Asn Gly Asp Phe<br>      2150                   2155                  2160 | 3024 |
| AAC AAC GGC CTG ACC TGC TGG AAC GTG AAG GGC CAC GTG GAC GTG CAG<br>Asn Asn Gly Leu Thr Cys Trp Asn Val Lys Gly His Val Asp Val Gln<br>2165                 2170                  2175                2180 | 3072 |
| CAG AGC CAC CAC CGC AGC GAC CTG GTG ATC CCC GAG TGG GAG GCC GAG<br>Gln Ser His His Arg Ser Asp Leu Val Ile Pro Glu Trp Glu Ala Glu<br>              2185                  2190                2195 | 3120 |
| GTG AGC CAG GCC GTG CGC GTG TGC CCC GGC TGC GGC TAC ATC CTG CGC<br>Val Ser Gln Ala Val Arg Val Cys Pro Gly Cys Gly Tyr Ile Leu Arg<br>      2200                   2205                  2210 | 3168 |
| GTG ACC GCC TAC AAG GAG GGC TAC GGC GAG GGC TGC GTG ACC ATC CAC<br>Val Thr Ala Tyr Lys Glu Gly Tyr Gly Glu Gly Cys Val Thr Ile His<br>              2215                  2220                2225 | 3216 |
| GAG ATC GAG AAC AAC ACC GAC GAG CTG AAG TTC AAG AAC CGC GAG GAG<br>Glu Ile Glu Asn Asn Thr Asp Glu Leu Lys Phe Lys Asn Arg Glu Glu<br>      2230                   2235                  2240 | 3264 |
| GAG GAG GTG TAC CCC ACC GAC ACC GGC ACC TGC AAC GAC TAC ACC GCC<br>Glu Glu Val Tyr Pro Thr Asp Thr Gly Thr Cys Asn Asp Tyr Thr Ala<br>2245                 2250                  2255                2260 | 3312 |
| CAC CAG GGC ACC GCC GGC TGC GCC GAC GCC TGC AAC AGC CGC AAC GCC<br>His Gln Gly Thr Ala Gly Cys Ala Asp Ala Cys Asn Ser Arg Asn Ala<br>              2265                  2270                2275 | 3360 |
| GGC TAC GAG GAC GCC TAC GAG GTG GAC ACC ACC GCC AGC GTG AAC TAC<br>Gly Tyr Glu Asp Ala Tyr Glu Val Asp Thr Thr Ala Ser Val Asn Tyr<br>      2280                   2285                  2290 | 3408 |
| AAG CCC ACC TAC GAG GAG GAG ACC TAC ACC GAC GTG CGC CGC GAC AAC<br>Lys Pro Thr Tyr Glu Glu Glu Thr Tyr Thr Asp Val Arg Arg Asp Asn<br>              2295                  2300                2305 | 3456 |
| CAC TGC GAG TAC GAC CGC GGC TAC GTG AAC TAC CCC CCC GTG CCC GCC<br>His Cys Glu Tyr Asp Arg Gly Tyr Val Asn Tyr Pro Pro Val Pro Ala<br>      2310                   2315                  2320 | 3504 |
| GGC TAC GTG ACC AAG GAG CTG GAG TAC TTC CCC GAG ACC GAC ACC GTG<br>Gly Tyr Val Thr Lys Glu Leu Glu Tyr Phe Pro Glu Thr Asp Thr Val<br>2325                 2330                  2335                2340 | 3552 |
| TGG ATC GAG ATC GGC GAG ACC GAG GGC AAG TTC ATC GTG GAC AGC GTG<br>Trp Ile Glu Ile Gly Glu Thr Glu Gly Lys Phe Ile Val Asp Ser Val<br>              2345                  2350                2355 | 3600 |
| GAG CTG CTG CTG ATG GAG GAG TAG | 3624 |

Glu Leu Leu Leu Met Glu Glu
            2360

(2) INFORMATION FOR SEQ ID NO:8:

(i) SEQUENCE CHARACTERISTICS:
        (A) LENGTH: 1207 amino acids
        (B) TYPE: amino acid
        (D) TOPOLOGY: linear (ii) MOLECULE TYPE: protein (xi) SEQUENCE DESCRIPTION: SEQ ID NO:8:

Met Asp Leu Leu Pro Asp Ala Arg Ile Glu Asp Ser Leu Cys Ile Ala
 1               5                  10                  15

Glu Gly Asn Asn Ile Asp Pro Phe Val Ser Ala Ser Thr Val Gln Thr
            20                  25                  30

Gly Ile Asn Ile Ala Gly Arg Ile Leu Gly Val Leu Gly Val Pro Phe
        35                  40                  45

Ala Gly Gln Leu Ala Ser Phe Tyr Ser Phe Leu Val Gly Glu Leu Trp
    50                  55                  60

Pro Arg Gly Arg Asp Gln Trp Glu Ile Phe Leu Glu His Val Glu Gln
65                  70                  75                  80

Leu Ile Asn Gln Gln Ile Thr Glu Asn Ala Arg Asn Thr Ala Leu Ala
                85                  90                  95

Arg Leu Gln Gly Leu Gly Asp Ser Phe Arg Ala Tyr Gln Gln Ser Leu
            100                 105                 110

Glu Asp Trp Leu Glu Asn Arg Asp Asp Ala Arg Thr Arg Ser Val Leu
        115                 120                 125

Tyr Thr Gln Tyr Ile Ala Leu Glu Leu Asp Phe Leu Asn Ala Met Pro
    130                 135                 140

Leu Phe Ala Ile Arg Asn Gln Glu Val Pro Leu Leu Met Val Tyr Ala
145                 150                 155                 160

Gln Ala Ala Asn Leu His Leu Leu Leu Arg Asp Ala Ser Leu Phe
                165                 170                 175

Gly Ser Glu Phe Gly Leu Thr Ser Gln Glu Ile Gln Arg Tyr Tyr Glu
            180                 185                 190

Arg Gln Val Glu Arg Thr Arg Asp Tyr Ser Asp Tyr Cys Val Glu Trp
        195                 200                 205

Tyr Asn Thr Gly Leu Asn Ser Leu Arg Gly Thr Asn Ala Ala Ser Trp
    210                 215                 220

Val Arg Tyr Asn Gln Phe Arg Arg Asp Leu Thr Leu Gly Val Leu Asp
225                 230                 235                 240

Leu Val Ala Leu Phe Pro Ser Tyr Asp Thr Arg Thr Tyr Pro Ile Asn
                245                 250                 255

Thr Ser Ala Gln Leu Thr Arg Glu Val Tyr Thr Asp Ala Ile Gly Ala
            260                 265                 270

Thr Gly Val Asn Met Ala Ser Met Asn Trp Tyr Asn Asn Ala Pro
        275                 280                 285

Ser Phe Ser Ala Ile Glu Ala Ala Ile Arg Ser Pro His Leu Leu
    290                 295                 300

Asp Phe Leu Glu Gln Leu Thr Ile Phe Ser Ala Ser Ser Arg Trp Ser
305                 310                 315                 320

Asn Thr Arg His Met Thr Tyr Trp Arg Gly His Thr Ile Gln Ser Arg
                325                 330                 335

Pro Ile Gly Gly Gly Leu Asn Thr Ser Thr His Gly Ala Thr Asn Thr

-continued

```
            340                 345                 350
Ser Ile Asn Pro Val Thr Leu Arg Phe Ala Ser Arg Asp Val Tyr Arg
            355                 360                 365
Thr Glu Ser Tyr Ala Gly Val Leu Leu Trp Gly Ile Tyr Leu Glu Pro
        370                 375                 380
Ile His Gly Val Pro Thr Val Arg Phe Asn Phe Thr Asn Pro Gln Asn
385                 390                 395                 400
Ile Ser Asp Arg Gly Thr Ala Asn Tyr Ser Gln Pro Tyr Glu Ser Pro
                405                 410                 415
Gly Leu Gln Leu Lys Asp Ser Glu Thr Glu Leu Pro Pro Glu Thr Thr
            420                 425                 430
Glu Arg Pro Asn Tyr Glu Ser Tyr Ser His Arg Leu Ser His Ile Gly
            435                 440                 445
Ile Ile Leu Gln Ser Arg Val Asn Val Pro Val Tyr Ser Trp Thr His
        450                 455                 460
Arg Ser Ala Asp Arg Thr Asn Thr Ile Gly Pro Asn Arg Ile Thr Gln
465                 470                 475                 480
Ile Pro Met Val Lys Ala Ser Glu Leu Pro Gln Gly Thr Thr Val Val
                485                 490                 495
Arg Gly Pro Gly Phe Thr Gly Gly Asp Ile Leu Arg Arg Thr Asn Thr
            500                 505                 510
Gly Gly Phe Gly Pro Ile Arg Val Thr Val Asn Gly Pro Leu Thr Gln
            515                 520                 525
Arg Tyr Arg Ile Gly Phe Arg Tyr Ala Ser Thr Val Asp Phe Asp Phe
        530                 535                 540
Phe Val Ser Arg Gly Gly Thr Thr Val Asn Asn Phe Arg Phe Leu Arg
545                 550                 555                 560
Thr Met Asn Ser Gly Asp Glu Leu Lys Tyr Gly Asn Phe Val Arg Arg
                565                 570                 575
Ala Phe Thr Thr Pro Phe Thr Phe Thr Gln Ile Gln Asp Ile Ile Arg
            580                 585                 590
Thr Ser Ile Gln Gly Leu Ser Gly Asn Gly Glu Val Tyr Ile Asp Lys
            595                 600                 605
Ile Glu Ile Ile Pro Val Thr Ala Thr Phe Glu Ala Glu Tyr Asp Leu
        610                 615                 620
Glu Arg Ala Gln Glu Ala Val Asn Ala Leu Phe Thr Asn Thr Asn Pro
625                 630                 635                 640
Arg Arg Leu Lys Thr Asp Val Thr Asp Tyr His Ile Asp Gln Val Ser
                645                 650                 655
Asn Leu Val Ala Cys Leu Ser Asp Glu Phe Cys Leu Asp Glu Lys Arg
            660                 665                 670
Glu Leu Leu Glu Lys Val Lys Tyr Ala Lys Arg Leu Ser Asp Glu Arg
            675                 680                 685
Asn Leu Leu Gln Asp Pro Asn Phe Thr Ser Ile Asn Lys Gln Pro Asp
        690                 695                 700
Phe Ile Ser Thr Asn Glu Gln Ser Asn Phe Thr Ser Ile His Glu Gln
705                 710                 715                 720
Ser Glu His Gly Trp Trp Gly Ser Glu Asn Ile Thr Ile Gln Glu Gly
                725                 730                 735
Asn Asp Val Phe Lys Glu Asn Tyr Val Thr Leu Pro Gly Thr Phe Asn
            740                 745                 750
Glu Cys Tyr Pro Thr Tyr Leu Tyr Gln Lys Ile Gly Glu Ser Glu Leu
            755                 760                 765
```

-continued

```
Lys Ala Tyr Thr Arg Tyr Gln Leu Arg Gly Tyr Ile Glu Asp Ser Gln
770                 775                 780
Asp Leu Glu Ile Tyr Leu Ile Arg Tyr Asn Ala Lys His Glu Thr Leu
785                 790                 795                 800
Asp Val Pro Gly Thr Glu Ser Leu Trp Pro Leu Ser Val Glu Ser Pro
            805                 810                 815
Ile Gly Arg Cys Gly Glu Pro Asn Arg Cys Ala Pro His Phe Glu Trp
            820                 825                 830
Asn Pro Asp Leu Asp Cys Ser Cys Arg Asp Gly Glu Lys Cys Ala His
            835                 840                 845
His Ser His His Phe Ser Leu Asp Ile Asp Val Gly Cys Thr Asp Leu
850                 855                 860
His Glu Asn Leu Gly Val Trp Val Phe Lys Ile Lys Thr Gln Glu
865                 870                 875                 880
Gly His Ala Arg Leu Gly Asn Leu Glu Phe Ile Glu Glu Lys Pro Leu
                885                 890                 895
Leu Gly Glu Ala Leu Ser Arg Val Lys Arg Ala Glu Lys Lys Trp Arg
            900                 905                 910
Asp Lys Arg Glu Lys Leu Gln Leu Glu Thr Lys Arg Val Tyr Thr Glu
            915                 920                 925
Ala Lys Glu Ala Val Asp Ala Leu Phe Val Asp Ser Gln Tyr Asp Arg
930                 935                 940
Leu Gln Ala Asp Thr Asn Ile Gly Met Ile His Ala Ala Asp Lys Leu
945                 950                 955                 960
Val His Arg Ile Arg Glu Ala Tyr Leu Ser Glu Leu Pro Val Ile Pro
                965                 970                 975
Gly Val Asn Ala Glu Ile Phe Glu Glu Leu Glu Gly His Ile Ile Thr
            980                 985                 990
Ala Ile Ser Leu Tyr Asp Ala Arg Asn Val Val Lys Asn Gly Asp Phe
            995                 1000                1005
Asn Asn Gly Leu Thr Cys Trp Asn Val Lys Gly His Val Asp Val Gln
        1010                1015                1020
Gln Ser His His Arg Ser Asp Leu Val Ile Pro Glu Trp Glu Ala Glu
1025                1030                1035                1040
Val Ser Gln Ala Val Arg Val Cys Pro Gly Cys Gly Tyr Ile Leu Arg
                1045                1050                1055
Val Thr Ala Tyr Lys Glu Gly Tyr Gly Glu Gly Cys Val Thr Ile His
            1060                1065                1070
Glu Ile Glu Asn Asn Thr Asp Glu Leu Lys Phe Lys Asn Arg Glu Glu
        1075                1080                1085
Glu Glu Val Tyr Pro Thr Asp Thr Gly Thr Cys Asn Asp Tyr Thr Ala
        1090                1095                1100
His Gln Gly Thr Ala Gly Cys Ala Asp Ala Cys Asn Ser Arg Asn Ala
1105                1110                1115                1120
Gly Tyr Glu Asp Ala Tyr Glu Val Asp Thr Thr Ala Ser Val Asn Tyr
            1125                1130                1135
Lys Pro Thr Tyr Glu Glu Glu Thr Tyr Thr Asp Val Arg Arg Asp Asn
            1140                1145                1150
His Cys Glu Tyr Asp Arg Gly Tyr Val Asn Tyr Pro Pro Val Pro Ala
            1155                1160                1165
Gly Tyr Val Thr Lys Glu Leu Glu Tyr Phe Pro Glu Thr Asp Thr Val
            1170                1175                1180
```

-continued

```
Trp Ile Glu Ile Gly Glu Thr Glu Gly Lys Phe Ile Val Asp Ser Val
1185                1190                1195                1200

Glu Leu Leu Leu Met Glu Glu
                1205
```